(12) United States Patent
Okada et al.

(10) Patent No.: US 8,546,111 B2
(45) Date of Patent: Oct. 1, 2013

(54) MALTOTRIOSYL TRANSFERASE AND USE THEREOF

(75) Inventors: Masamichi Okada, Kakamigahara (JP); Shotaro Yamaguchi, Kakamigahara (JP); Miho Nagaya, Kakamigahara (JP)

(73) Assignee: Amano Enzyme Inc., Nagoya-shi (JP)

( * ) Notice: Subject to any disclaimer, the term of this patent is extended or adjusted under 35 U.S.C. 154(b) by 0 days.

(21) Appl. No.: 13/381,455

(22) PCT Filed: Mar. 20, 2010

(86) PCT No.: PCT/JP2010/054894
§ 371 (c)(1),
(2), (4) Date: Dec. 29, 2011

(87) PCT Pub. No.: WO2011/001722
PCT Pub. Date: Jan. 6, 2011

(65) Prior Publication Data
US 2012/0100253 A1 Apr. 26, 2012

(30) Foreign Application Priority Data

Jul. 1, 2009 (JP) .................................. 2009-156569

(51) Int. Cl.
*C12P 19/18* (2006.01)
*C12N 9/10* (2006.01)
*A23D 9/013* (2006.01)
*A21D 13/06* (2006.01)

(52) U.S. Cl.
USPC .............. 435/97; 435/193; 426/531; 426/549

(58) Field of Classification Search
None
See application file for complete search history.

(56) References Cited

FOREIGN PATENT DOCUMENTS

| JP | 2001-294601 A | 10/2001 |
| WO | WO-02/10361 A1 | 2/2002 |
| WO | WO-2008/001940 A1 | 1/2008 |

OTHER PUBLICATIONS

Alpha amylase [*Geobacillus* sp. WCH70], GenBank YO_002948858.1, Jun. 11, 2009, 3 pages.
Office Action dated Oct. 8, 2012, issued for the Chinese Patent Application No. 201080029335.6.
S. Tabata et al., "Electrochemical detection of reducing carbohydrates produced by the transferase action of yeast debranching enzyme on maltosaccharides," Carbohydrate Research, Pergamon, vol. 176, No. 2, May 15, 1988, pp. 245-251.
C.-H. Yang et al., "Cloning and characterization of a maltotriose-producing [alpha]-amylase gene from *Thermobifida fusca*," Journal of Industrial Microbiology & Biotechnology, vol. 34, No. 4, Jan. 9, 2007, pp. 325-330.
Supplementary European Search Report dated Nov. 22, 2012, issued for the corresponding European Patent Application No. 10793893.8.
Denpunkagaku no jiten, Asakura Publishing Co., Ltd., 2003, pp. 279-280.
K. Wako et. al., "Studies on Maltotriose- and Maltose-forming Amylases from *Streptomyces*," Denpun kagaku (= Journal of the Japanese Society of Starch Science), 25(2), 1978, pp. 155-161.
T. Usui et. al, "Transglycosylation reaction of maltotriose-forming amylase from *Streptomyces griseus*," Carbohydr. Res. 250, 1993, pp. 57-66.
S. Okada et. al, "Branching Enzyme from *Bacillus* sp.," Denpun kagaku (= Journal of the Japanese Society of Starch Science), 30(2), 1983, pp. 223-230.
Database UniProtKB/TrEMBL[online], Accession No. B1SUY3, May 20, 2008 uploaded.
International Search Report dated Apr. 27, 2010, issued for PCT/JP2010/054894.

*Primary Examiner* — David J Steadman
(74) *Attorney, Agent, or Firm* — Edwards Wildman Palmer LLP; James E. Armstrong, IV; Edmund J. Koundakjian

(57) ABSTRACT

The object is to provide a novel glycosyltransferase and the use thereof, the glycosyltransferase catalyzes transglucosylation of maltotriose units under conditions which can be employed for the processing of foods or the like. Provided is a maltotriosyl transferase which acts on polysaccharides and oligosaccharides having α-1,4 glucoside bonds, and has activity for transferring maltotriose units to saccharides, the maltotriosyl transferase acting on maltotetraose as substrate to give a ratio between the maltoheptaose production rate and maltotriose production rate of 9:1 to 10:0 at any substrate concentration ranging from 0.67 to 70% (w/v).

8 Claims, 7 Drawing Sheets

MALTOTRIOSYL TRANSFERASE AND USE THEREOF

TECHNICAL FIELD

The present invention relates to a maltotriosyl transferase and the use thereof, and specifically to a novel maltotriosyl transferase and a method for producing the same, the use of the enzyme in food production and processing, and a microorganism producing the enzyme. The present application claims priority based on Japanese Patent Application No. 2009-156569 filed on Jul. 1, 2009, and the content of the patent application is hereby incorporated by reference herein in its entirety.

BACKGROUND ART

Maltotriose-producing amylases heretofore known are the enzymes derived from *Microbacterium imperiale, Streptomyces griseus, Bacillus subtilis, Natronococcus* sp., and *Streptococcus bovis* (Non-Patent Document 1). However, among these enzymes, only the *Streptomyces griseus*-derived enzyme is reported about its involvement with transglucosylation. In addition, this enzyme catalyzes transglucosylation only when the substrate concentration is high (the sum of the donor and acceptor substrates is 19%, 40% (w/v)), while catalyzes hydrolysis reaction alone when the substrate concentration is low (1% (w/v)), and will not catalyze transglucosylation (Non-Patent Documents 2 and 3). In addition, the enzyme is poorly resistant to heat, and thus is not used for food processing purposes.

Examples of industrially used glycosyltransferase include α-glucosidase used for the production of isomaltooligosaccharide or nigerooligosaccharide, β-fructofuranosidase used for the production of fructo-oligosaccharide or lactosucrose, β-galactosidase used for the production of galactooligosaccharide, α-glucosyltransferase used for the production of palatinose, cyclodextringlucanotransferase used for the production of cyclodextrin or coupling sugar, and branching enzymes used for the production of highly branched cyclic dextrin. Among these, α-glucosidase and branching enzymes act on polysaccharides and oligosaccharides containing α-1,4 bonds to catalyze transglucosylation. α-glucosidase catalyzes transglucosylation of monosaccharides, and branching enzymes catalyze transglucosylation of oligosaccharides containing four or more sugars or polysaccharides. There is no known enzyme which specifically catalyzes transglucosylation of maltotriose which is a trisaccharide.

In processed food containing starch, retrogradation of starch causes serious problems such as deterioration of storage stability. Retrogradation of starch is caused mainly by retrogradation of amylose molecules contained in starch, more specifically association of amylose molecules accompanied by insolubilization (Non-Patent Document 4). As a result of research on retrogradation control through starch depolymerization, retrogradation control is now possible to some degree. However, such depolymerized starch loses its intrinsic properties. In addition, decomposed starch has higher reducing power, and thus can react with a protein or amino acid when heated together, which results in coloring of the starch. Therefore, these methods have found limited applications (Patent Document 1). In order to solve these problems, studies for controlling retrogradation of starch without depolymerization have been carried out. For example, branching enzymes which decompose α-1,4 bonds of starch and synthesize α-1,6 bonds by transfer reaction are studied, but they have poor heat resistance, and thus are not used as food processing enzymes.

PRIOR ART DOCUMENTS

Patent Documents

Patent Document 1: Japanese Unexamined Patent Application Publication No. 2001-294601

Non-Patent Documents

Non-Patent Document 1: "Denpun Kagakuno Jiten", Asakura Publishing Co., Ltd., p. 279-80 (2003)Non-Patent Document 2: Wakao et al, Journal of the Japanese Society of Starch Science, 25(2), p. 155-61 (1978) Non-Patent Document 3: Usui et al, Carbohydr. Res. 250, 57-66 (1993) Non-Patent Document 4: Okada et al, Journal of the Japanese Society of Starch Science, 30(2), p. 223-230 (1983) Non-Patent Document 5: Saito, and Miura. Biochim. Biophys. Acta, 72, 619-629 (1963)

SUMMARY OF THE INVENTION

Problems to be Solved by the Invention

The present invention is intended to provide a novel glycosyltransferase which catalyzes transglucosylation of maltotriose units under conditions which can be employed for the processing of foods or the like.

Means for Solving Problem

The inventors diligently made researches for solving the above-described problems. As a result of this, they have found that a microorganism belonging to the genus *Geobacillus* produces a maltotriosyl transferase which has the desired function. Furthermore, the inventors isolated and purified the maltotriosyl transferase, and have succeeded in determining the enzymatic chemical properties, and cloning the gene coding the enzyme (hereinafter referred to as, "the present gene"). In addition, they established the method for producing a maltotriosyl transferase through the introduction of the present gene and fragments of the present gene into an appropriate host. The present invention has been accomplished based on these results, and its aspects are as follows. [1] A maltotriosyl transferase which acts on polysaccharides and oligosaccharides having α-1,4 glucoside bonds to transfer maltotriose units to saccharides, the maltotriosyl transferase acting on maltotetraose as substrate to give a ratio between the maltoheptaose production rate and maltotriose production rate of 9:1 to 10:0 at any substrate concentration ranging from 0.67 to 70% (w/v). [2] The maltotriosyl transferase according to [1], wherein the maltotriosyl transferase is an enzyme derived from a microorganism. [3] The maltotriosyl transferase according to [1], wherein the maltotriosyl transferase is an enzyme derived from a microorganism belonging to the genus *Geobacillus*. [4] The maltotriosyl transferase according to [3], wherein the microorganism belonging to the genus *Geobacillus* is *Geobacillus* sp. APC9669 (accession number NITE BP-770). [5] A maltotriosyl transferase comprising the following enzymatic chemical properties:

(1) action: acts on polysaccharides and oligosaccharides having α-1,4 glucoside bonds as a binding mode to transfer maltotriose units to saccharides;

(2) substrate specificity: acts on soluble starch, amylose, amylopectin, maltotetraose, maltopentaose, and maltohexaose, while does not act on α-cyclodextrin, β-cyclodextrin, γ-cyclodextrin, maltotriose, and maltose; and (3) molecular weight: about 83,000 (SDS-PAGE). [6] An enzyme product comprising the maltotriosyl transferase of any one of [1] to [5] as an active ingredient. [7] A microorganism having a capability to produce maltotriosyl transferase, the microorganism being *Geobacillus* sp. APC9669 (accession number NITE BP-770) or its mutant strain. [8] A maltotriosyl transferase comprising the amino acid sequence set forth in SEQ ID NO: 8, or its fragment exhibiting maltotriosyl transferase activity. [9] The maltotriosyl transferase according to [8] coded by a DNA comprising the sequence set forth in SEQ ID NO: 6. [10] A maltotriosyl transferase gene comprising any of the DNAs selected from the group consisting of the following (a) to (e): (a) DNA coding the amino acid sequence set forth in SEQ ID NO: 7 or 8; (b) DNA comprising the sequence set forth in SEQ ID NO: 6; (c) DNA hybridizing with the complementary sequence of the sequence set forth in SEQ ID NO: 6 under stringent conditions; (d) DNA which is a degenerate of the DNA sequence of the sequence set forth in SEQ ID NO: 6; (e) DNA coding comprising a sequence including substitution, deletion, insertion, addition, or inversion of one or a plurality of bases with reference to the sequence set forth in SEQ ID NO: 6, and coding a protein having maltotriosyl transferase activity. [11] A recombinant vector comprising the maltotriosyl transferase gene of [10]. [12] The recombinant vector of [11], which is an expression vector. [13] A transformant into which the maltotriosyl transferase gene of [10] has been introduced. [14] A transformant into which the recombinant vector of [11] or [12] has been introduced.

[15] The transformant according to [13] or [14], which is a bacterial cell, a yeast cell, or a fungal cell. [16] A method for producing a maltotriosyl transferase, comprising the following steps (1) and (2), or the steps (i) and (ii): (1) culturing a microorganism belonging to the genus *Geobacillus* having a capability to produce a maltotriosyl transferase; and (2) collecting the maltotriosyl transferase from the culture solution and/or bacterial cells after culturing. (i) culturing the transformant of any one of [13] to [15] under conditions suitable for the production of the protein coded by the maltotriosyl transferase gene; and (ii) collecting the protein thus produced. [17] The production method according to [16], wherein the microorganism belonging to the genus *Geobacillus* is *Geobacillus* sp. APC9669. [18] A use of the enzyme of any one of [1] to [5], or the enzyme product of [6] for producing and processing a food containing a polysaccharide or oligosaccharide having α-1,4 glucoside bonds. [19] A food or food ingredient which has been improved in its function by the use of the enzyme of any one of [1] to [5], or the enzyme product of [6].

Figure 1:
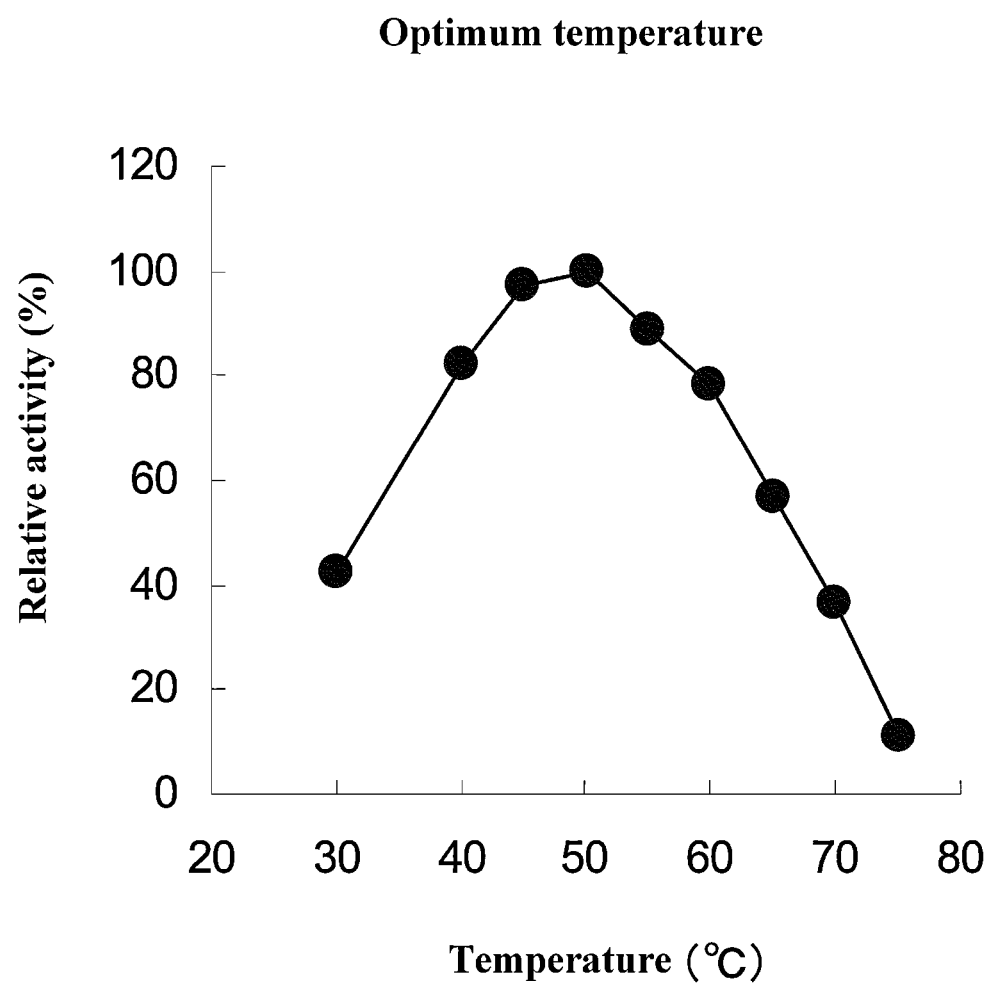
FIG. 1 is a graph showing the optimum temperature for the maltotriosyl transferase derived from *Geobacillus* sp. APC9669.

DETAILED DESCRIPTION OF THE INVENTION (Term) In the present invention, the term "DNA coding a protein" refers to the DNA which gives the protein upon expression, more specifically the DNA having a base sequence corresponding to the amino acid sequence of the protein. Accordingly, codon degeneracy is taken into consideration.

In the present description, the term "isolated" may be replaced with "purified". When the enzyme of the present invention (maltotriosyl transferase) is derived from a natural material, the term "isolated" used for the enzyme means that the enzyme is substantially free of components of the natural material other than the enzyme (specifically substantially free of contaminant protein). Specifically, for example, in the isolated enzyme of the present invention, the content of contaminant proteins is less than about 20%, preferably less than about 10%, more preferably less than about 5%, and even more preferably less than about 1% in the weight equivalence. On the other hand, when the enzyme of the present invention is prepared by a genetic engineering technique, the term "isolated" means that the enzyme is substantially free of other components derived from the host cells or culture solution used. Specifically, for example, in the isolated enzyme of the present invention, the content of contaminant components is less than about 20%, preferably less than about 10%, more preferably less than about 5%, and even more preferably less than about 1% in the weight equivalence. In the present description, the simple term "maltotriosyl transferase" means "isolated maltotriosyl transferase", unless it is evident that the term has a different meaning. The same applies to the term "the present enzyme" used in place of maltotriosyl transferase.

When the term "isolated" is used for a native DNA, the term typically means that the DNA is separated from other nucleic acids coexisting with the DNA in its natural state. However, the DNA may contain some of other nucleic acid components, such as a flanking nucleic acid sequence of the DNA in its natural state (for example, the sequence of the promoter region or the terminator sequence). For example, when a genome DNA is in an "isolated" state, it is preferably substantially free of other DNA components which coexist with the DNA in its natural state. On the other hand, when a DNA prepared by a genetic engineering technique, such as a cDNA molecule, is in an "isolated" state, it is preferably substantially free of cell components or culture solution. In addition, when a DNA prepared by chemical synthesis is in an "isolated" state, it is preferably substantially free of precursors (raw materials) such as dNTP or chemical substances used during synthesis. In the present description, the simple term "DNA" means an isolated DNA, unless it is evident that the term has a different meaning.

(Maltotriosyl transferase and bacterium producing the same) A first aspect of the present invention is to provide a maltotriosyl transferase (hereinafter, also referred to as "the present enzyme") and a bacterium producing the same. As described in the below-described Examples, the inventors carried out dedicated research, and have found that *Geobacillus* sp. APC9669 produces a maltotriosyl transferase. Furthermore, they have succeeded in isolating and producing the maltotriosyl transferase, and, as described below, in determining the enzymatic chemical properties of the enzyme.

(1) Action The present enzyme is a maltotriosyl transferase, and acts on polysaccharides and oligosaccharides having α-1,4 glucoside bonds as a binding mode to transfer maltotriose units to saccharides.

(2) Substrate specificity The present enzyme favorably acts on soluble starch, amylose, amylopectin, maltotetraose, maltopentaose, and maltohexaose. On the other hand, the present enzyme does not act on α-cyclodextrin, β-cyclodextrin, γ-cyclodextrin, maltotriose, and maltose.

(3) Molecular weight The molecular weight of the present enzyme is about 83,000 (by SDS-PAGE).

(4) Optimum temperature The optimum temperature for the present enzyme is about 50° C. The present enzyme exhibits high activity in the temperature range of about 45° C. to 55° C. The optimum temperature was calculated by the below-described method for measuring maltotriosyl transferase activity (in 10 mmol/L MES buffer solution (pH 6.5)).

(5) Optimum pH The optimum pH for the present enzyme is about 7.5. The present enzyme exhibits high activity in the pH range of about 6.5 to 8.0. The optimum pH is determined based on, for example, the measurement in a universal buffer solution.

(6) Thermostability The present enzyme exhibits stable activity at 65° C. or lower. The present enzyme keeps 90% or higher level of activity even after treatment for 30 minutes at 65° C. in a 10 mmol/L MES buffer solution (pH 6.5).

(7) pH stability The present enzyme exhibits stable activity in a wide pH range of 5.0 to 10.0. More specifically, the enzyme keeps 85% or higher level of activity after treatment for 30 minutes at 40° C., as long as the pH of the enzyme solution used for the treatment is within the above range.

(8) Isoelectric point The isoelectric point of the present enzyme is about 4.5 (by Ampholine electrophoresis).

As shown in the below-described Examples, when the maltotriosyl transferase produced by *Geobacillus* sp. APC9669 acts on maltotetraose as substrate, it gives a ratio between the maltoheptaose production rate and maltotriose production rate of 9:1 to 10:0 at any substrate concentration ranging from 0.67 to 70% (w/v), wherein maltoheptaose is a transglycosylation product and maltotriose is a decomposition product, respectively. In other words, the rate of transglucosylation is far higher over the wide substrate concentration range, and the maltoheptaose production rate was 90% or more, taking the sum of the maltoheptaose and maltotriose production rates as 100%. The rates were compared based on the molar ratios of the products.

As described above, details about the properties of the present enzyme obtained herein have been revealed. As a result of this, it has been found that the present enzyme has high heat resistance and high substrate specificity. Accordingly, the present enzyme is suitable for food processing.

The present enzyme is preferably a maltotriosyl transferase derived from *Geobacillus* sp. APC9669. The term "maltotriosyl transferase derived from *Geobacillus* sp. APC9669" in this case means a maltotriosyl transferase produced by *Geobacillus* sp. APC9669 (wild strain or mutant strain), or a maltotriosyl transferase obtained by a genetic engineering technique using the maltotriosyl transferase gene of *Geobacillus* sp. APC9669 (wild strain or mutant strain). Accordingly, "maltotriosyl transferase derived from *Geobacillus* sp. APC9669" includes the recombinants produced by host microorganisms into which the maltotriosyl transferase gene (or the modified version of the gene) obtained from *Geobacillus* sp. APC9669, "*Geobacillus* sp. APC9669 has been introduced.

For convenience of explanation, *Geobacillus* sp. APC9669 which is the source of the present enzyme is referred herein the bacterium producing the present enzyme. The APC9669 strain is deposited on the below-described depository, and is readily available therefrom. Depository institution: Patent Microorganisms Depository, NITE Biotechnology Development Center (2-5-8, Kazusakamatari, Kisarazu-shi, Chiba, 292-0818, Japan) Date of deposit (date of receipt): Jun. 2, 2009

Accession number: NITE BP-770

The maltotriosyl transferase of the present invention according to one embodiment contains the amino acid sequence set forth in SEQ ID NO: 8. This amino acid sequence is the amino acid sequence set forth in SEQ ID NO: 7 excluding the signal peptide portion. The amino acid sequence set forth in SEQ ID NO: 7 was deduced from the base sequence (SEQ ID NO: 6) of the gene obtained by cloning *Geobacillus* sp. APC9669. In general, when the amino acid sequence of a certain protein is partially modified, the modified protein may have equivalent function to the unmodified protein. More specifically, modification of the amino acid sequence does not substantially influence the function of the protein, and thus the function of the protein may be maintained before and after the modification. Accordingly, another embodiment of the present invention provides a protein which is composed of an amino acid sequence equivalent to the amino acid sequence set forth in SEQ ID NO: 8, and has maltotriosyl transferase activity (hereinafter, also referred to as "equivalent protein"). The term "equivalent amino acid sequence" in this case means an amino acid sequence which is partially different from the amino acid sequence set forth in SEQ ID NO: 8, but the difference does not substantially influence the function of the protein (maltotriosyl transferase activity). The term "maltotriosyl transferase activity" means the activity for polysaccharides and oligosaccharides having α-1,4 glucoside bonds as a binding mode to transfer the maltotriose units to saccharides. The degree of the activity is not particularly limited as long as the function of a maltotriosyl transferase can be exhibited, but is preferably equivalent to or higher than that of the protein composed of the amino acid sequence set forth in SEQ ID NO: 8.

The term "partial difference in the amino acid sequence" typically means mutation (change) in the amino acid sequence caused by deletion or substitution of one to several (up to, for example, 3, 5, 7, or 10) amino acids composing the amino acid sequence, or addition, insertion, or combination thereof of one to several (up to, for example, 3, 5, 7, or 10) amino acids. The difference in the amino acid sequence is acceptable as long as the maltotriosyl transferase activity is maintained (the activity may be varied to a degree). As long as the conditions are satisfied, the position of the difference in the amino acid sequence is not particularly limited, and the difference may arise in a plurality of positions. The term "plurality" means, for example, a number corresponding to less than about 30%, preferably less than about 20%, more preferably less than about 10%, even more preferably less than about 5% of the total amino acids, and most preferably less than about 1%. More specifically, the equivalent protein has, for example, about 70% or more, preferably about 80% or more, even more preferably about 90% or more, even more preferably about 95% or more, and most preferably about 99% or more identity with the amino acid sequence set forth in SEQ ID NO: 8.

Preferably, the equivalence protein is obtained by causing conservative amino acid substitution in an amino acid residue which is not essential for maltotriosyl transferase activity.

The term "conservative amino acid substitution" means the substitution of an amino acid residue with another amino acid residue having a side chain with similar properties. Amino acid residues are classified into several families according to their side chains, such as basic side chains (for example, ricin, arginine, and histidine), acidic side chains (for example, aspartic acid and glutamic acid), uncharged polar side chains (for example, glycine, asparagine, glutamine, serine, threonine, tyrosine, and cysteine), nonpolar side chains (for example, alanine, valine, leucine, isoleucine, proline, phenylalanine, methionine, and tryptophan), β branched side chains (for example, threonine, valine, and isoleucine), and aromatic side chains (for example, tyrosine, phenylalanine, tryptophan, and histidine). Conservative amino acid substitution is preferably the substitution between amino acid residues in one family.

The "equivalent protein" may have additional properties. For example, the equivalent protein may have higher stability than the protein composed of the amino acid sequence set forth in SEQ ID NO: 8, may perform a different function performed only at low temperatures and/or high temperatures, or may have a different optimum pH.

The identity (%) between the two amino acid sequences may be determined by, for example, the following procedure. Firstly, the two sequences are aligned for optimal comparison (for example, a gap may be introduced into the first sequence thereby optimizing the alignment with the second sequence). When the molecule at the specific position in the first sequence (amino acid residue) is the same as the molecule at the corresponding position in the second sequence, the molecules at the positions are regarded as identical. The sequence identity is the function of the number of the identical positions common to the two sequences (more specifically, identity (%)=number of identical positions/total number of positions×100), and preferably the number and size of the gaps required for the optimization of the alignment are taken into consideration. Comparison of the two sequences and determination of the identity are achieved using a mathematic algorithm. Specific examples of the mathematic algorithm usable for the comparison of the sequences include, but not limited to, the algorithm described in Karlin and Altschul (1990) Proc. Natl. Acad. Sci. USA 87:2264-68, and modified in Karlin and Altschul (1993) Proc. Natl. Acad. Sci. USA 90:5873-77. These algorithms are incorporated into NBLAST Program and XBLAST Program (version 2.0) described in Altschul et al. (1990) J. Mol. Biol. 215:403-10. For example, under XBLAST Program, when BLAST polypeptide is searched under conditions that score=50 and wordlength=3, an amino acid sequence with a high identity can be obtained. Gapped BLAST described in Altschul et al. (1997), Amino Acids Research 25(17): 3389-3402 can be used for obtaining a gap alignment for comparison. When BLAST and Gapped BLAST are used, default parameters of corresponding programs (for example, XBLAST and NBLAST) may be used. For more detailed information, see, for example, the website of NCBI. Other examples of the mathematic algorithm usable for the comparison of the sequences include the algorithm described in Myersand Miller (1988) Comput Appl BioSci. 4: 11-17. These algorithms are incorporated into, for example, ALIGN Program usable in GENESTREAM Network Server (IGH Montpellier, France) or ISREC Server. When ALIGN program is used for the comparison of amino acid sequences, for example, a PAM120 weight residue table is used, wherein the gap length penalty is 12, and the gap penalty is 4. The identity between the two amino acid sequences is determined according to GAP Program of GCG software package using Blossom 62 matrix or PAM250 matrix, wherein the gap weight is 12, 10, 8, 6, or 4, and the gap length weight is =2, 3, or 4.

The present enzyme may be a portion of a larger protein (for example, a fused protein). Examples of the sequence added to a fused protein include the sequences useful for purification of multiple histidine residues, and addition sequences which ensures stability in recombination production.

The present enzyme having the above-described amino acid sequence is readily prepared by a genetic engineering technique. For example, an appropriate host cell (for example, *Escherichia coli*) is transformed by a DNA coding the present enzyme, and the protein expressed in the transformant is collected, and thereby preparing the present enzyme. The collected protein is treated as appropriate according to the intended use. The present enzyme thus obtained as a recombinant protein may be subjected to various modifications. For example, the present enzyme composed of a recombinant protein linked to any peptide or protein can be obtained by producing a recombinant protein using a vector into which a DNA coding the present enzyme has been inserted together with other appropriate DNA. In addition, modification for causing addition of a sugar chain and/or a lipid, or N- or C-terminal processing may be carried out. These modifications allow, for example, extraction of a recombinant protein, simplification of purification, or addition of biological functions.

(Maltotriosyl transferase gene) A second aspect of the present invention relates to a maltotriosyl transferase gene. The gene according to one embodiment of the present invention contains the DNA coding the amino acid sequence set forth in SEQ ID NO: 7 or 8. A specific example of the embodiment is the DNA composed of the base sequence set forth in SEQ ID NO: 6.

In general, when a DNA coding a certain protein is partially modified, the protein coded by the modified DNA may have the equivalent function to the protein coded by the unmodified DNA. More specifically, modification of the DNA sequence does not substantially influence the function of the protein coded, so that the function of the coded protein may be maintained before and after the modification. Therefore, another embodiment of the present invention provides a DNA (hereinafter, also referred to as "equivalent DNA") which has an equivalent base sequence to the base sequence set forth in SEQ ID NO: 6, and codes a protein having maltotriosyl transferase activity. The term "equivalent base sequence" in this case means a base sequence which is partially different from the nucleic acid set forth in SEQ ID NO: 6, but the difference exerts no substantial influence on the function (in this case, maltotriosyl transferase activity) of the protein coded.

A specific example of the equivalent DNA is a DNA which hybridizes with the base sequence complementary to the base sequence set forth in SEQ ID NO: 6 under stringent conditions. The term "stringent conditions" in this case means the conditions under which a so-called specific hybrid is formed, but nonspecific hybrid will not be formed. Such stringent conditions are known to those skilled in the art, and may be established consulting with, for example, Molecular Cloning (Third Edition, Cold Spring Harbor Laboratory Press, New York) and Current protocols in molecular biology (edited by Frederick M. Ausubel et al., 1987). The stringent conditions include, for example, incubation at about 42° C. to 50° C. in a hybridization solution (50% formamide, 10×SSC (0.15 M NaCl, 15 mM sodium citrate, pH 7.0), 5×Denhardt solution, 1% SDS, 10% dextran sulfate, 10 μg/ml modified salmon sperm DNA, and 50 mM phosphoric acid buffer (pH 7.5)), followed by washing with 0.1×SSC and 0.1% SDS at about 65° C. to 70° C. Under even more preferred stringent conditions, for example, the hybridization solution is 50% formamide, 5×SSC (0.15 M NaCl, 15 mM sodium citrate, pH 7.0), 1×Denhardt solution, 1% SDS, 10% dextran sulfate, 10 μg/ml modified salmon sperm DNA, and 50 mM phosphoric acid buffer (pH 7.5)).

Specific examples of the equivalent DNA include a DNA which is composed of a base sequence including substituted, deletion, insertion, addition, or inversion of one or a plurality of (preferably one to several) bases with reference to the base sequence set forth in SEQ ID NO: 6, and codes a protein having maltotriosyl transferase activity. The substitution or deletion of the base may arise in a plurality of regions. The term "a plurality of" means, for example, from 2 to 40 bases, preferably from 2 to 20 bases, and more preferably from 2 to 10 bases, though the number varies depending on the position and type of the amino acid residue in the steric structure of the protein coded by the DNA. The above-described equivalent DNA is obtained by, for example, modifying the DNA having the base sequence set forth in SEQ ID NO: 6 by restriction enzyme treatment, treatment with exonuclease or DNA ligase, or mutagenesis such as site-directed mutagenesis (Molecular Cloning, Third Edition, Chapter 13, Cold Spring Harbor Laboratory Press, New York) or random mutagenesis (Molecular Cloning, Third Edition, Chapter 13, Cold Spring Harbor Laboratory Press, New York), so as to include substitution, deletion, insertion, addition, and/or inversion of the base. Alternatively, the equivalent DNA may also be obtained by any other method such as ultraviolet irradiation. Other examples of the equivalent DNA include DNAs having the above-described difference in the bases due to polymorphism as typified by SNP (single nucleotide polymorphism).

The gene of the present invention may be prepared in an isolated state using, for example, standard genetic engineering technique, molecular biological technique, or biochemical technique, in consultation with the sequence information disclosed in the present description or the sequence list attached thereto. Specifically, the gene may be prepared from the genomic DNA library or cDNA library of *Geobacillus* sp. APC9669, or the intracellular extract of *Geobacillus* sp. APC9669, using as appropriate an oligonucleotide probe primer which can specifically hybridizes with the gene of the present invention. The oligonucleotide probe primer is readily synthesized using, for example, a commercially available automatic DNA synthesizer. The method for constructing the library used for the preparation of the gene of the present invention may refer to, for example, Molecular Cloning, Third Edition, Cold Spring Harbor Laboratory Press, New York.

For example, a gene having the base sequence set forth in SEQ ID NO: 6 may be isolated by the hybridization method using the whole or a portion of the base sequence or its complementary sequence as the probe. Alternatively, the gene may be amplified and isolated by nucleic acid amplification reaction (for example PCR) using a synthetic oligonucleotide primer designed so as to specifically hybridize with a portion of the base sequence. Alternatively, the intended gene may be obtained by chemical synthesis, based on the information on the amino acid sequence set forth in SEQ ID NO: 7 or the base sequence set forth in SEQ ID NO: 6 (reference: Gene, 60(1), p. 115-127 (1987)).

An example of the method for obtaining the gene of the present invention is described below. Firstly, the present enzyme (maltotriosyl transferase) is isolated and purified from *Geobacillus* sp. APC9669, thereby obtaining information on the partial amino acid sequence. The partial amino acid sequence is determined by, for example, the purified maltotriosyl transferase is directly subjected to Edman degradation according to an ordinary method [Journal of Biological Chemistry, vol. 256, p. 7990 to 7997 (1981)], and then to amino acid sequence analysis [Protein Sequencer 476A, Applied Biosystems]. It is effective that limited proteolysis is carried out by the action of a proteolytic enzyme, the peptide fragment thus obtained is separated and purified, and the purified peptide fragment thus obtained is subjected to amino acid sequence analysis.

Based on the partial amino acid sequence information thus obtained, a maltotriosyl transferase gene is cloned. For example, the cloning may use a hybridization method or PCR. When the hybridization method is used, for example, the method described in Molecular Cloning (Third Edition, Cold Spring Harbor Laboratory Press, New York) may be used.

When the PCR method is used, the following method may be used. Firstly, using the genome DNA of a microorganism producing a maltotriosyl transferase as template, PCR reaction is carried out using a synthetic oligonucleotide primer designed based on the information concerning the partial amino acid sequence, thereby obtaining the desired gene fragment. The PCR method is carried out in accordance with the method described in "PCR Technology (edited by Erlich H A, Stocktonpress, 1989)". Furthermore, when the base sequence of the amplified DNA fragment is determined using a commonly used method, such as the dideoxy chain terminator method, a sequence corresponding to the partial amino acid sequence of a maltotriosyl transferase is found in addition to the sequence of the synthetic oligonucleotide primer in the determined sequence, and thus a part of the desired maltotriosyl transferase gene is obtained. Furthermore, the gene coding the full length of the maltotriosyl transferase can be cloned by, for example, hybridization using the gene fragment thus obtained as a probe.

In the below-described example, the sequence of the gene coding the maltotriosyl transferase produced by *Geobacillus* sp. APC9669 was determined using the PCR method. The entire base sequence of the gene coding the maltotriosyl transferase derived from *Geobacillus* sp. APC9669 is set forth in SEQ ID NO: 6. Furthermore, the amino acid sequence coded by the base sequence was determined (SEQ ID NO: 7). In addition to the base sequence set forth in SEQ ID NO: 6, there are a plurality of base sequences which correspond to the amino acid sequence set forth in SEQ ID NO: 7.

Using the whole or a portion of the maltotriosyl transferase gene (SEQ ID NO: 6), the entire base sequence of which has been revealed, as the hybridization probe, a DNA having high homology to the maltotriosyl transferase gene set forth in SEQ ID NO: 6 can be chosen from the genomic DNA library or cDNA library of the microorganism producing other maltotriosyl transferase.

The primer for PCR can be designed in the same manner. The PCR reaction using the primer allows the detection of gene fragments having high homology to the above-described maltotriosyl transferase gene, and acquisition of the entire gene.

Whether the gene obtained codes a protein having maltotriosyl transferase activity or not may be ascertained by producing the protein of the gene, and measuring its maltotriosyl transferase activity. Alternatively, whether the gene obtained codes a protein having maltotriosyl transferase activity or not may be judged by comparing the base sequence of the gene (or the amino acid sequence coded) with the base sequence of the above-described maltotriosyl transferase gene (or the amino acid sequence coded), thereby determining the gene structure and homology.

The elucidation of the primary structure and gene structure allows the acquisition of a modified maltotriosyl transferase (gene including substitution, deletion, insertion, addition, or inversion of one or a plurality of amino acid residues) through the introduction of random mutation or site-specific mutation. As a result of this, obtained is a gene which has maltotriosyl transferase activity, but codes a maltotriosyl transferase having different properties such as optimum temperature, stable temperature, optimum pH, stable pH, and substrate specificity. In addition, a modified maltotriosyl transferase is produced by genetic engineering technique.

The introduction of mutation is carried out in consideration of, for example, the characteristic sequence in the gene sequence. The consideration to the characteristic sequence is given by, for example, considering the prediction of the steric structure of the protein, and homology to known proteins.

Examples of the method for introducing random mutation include chemical treatment of DNA such as a method of causing transition mutation for converting cytosine base to uracil base by the action of sodium hydrogensulfite [Proceedings of the National Academy of Sciences of the USA, vol. 79, p. 1408 to 1412 (1982)], biochemical methods such as a method of causing base substitution during synthesis of a double-strand in the presence of [α-S]dNTP [Gene, vol. 64, p. 313 to 319 (1988)], and PCR methods such as a method of carrying out PCR in a reaction system containing manganese, thereby decreasing the accuracy of nucleotide uptake [Analytical Biochemistry, vol. 224, p. 347 to 353 (1995)].

Examples of the method of introducing site-specific mutation include a method of using amber mutation [gapped duplex method, Nucleic Acids Research, vol. 12, vol. 24, p. 9441 to 9456 (1984)], a method using the restricted enzyme recognition site [Analytical Biochemistry, vol. 200, p. 81 to 88 (1992), Gene, vol. 102, p. 67 to 70 (1991)], a method of using dut (dUTPase) and ung (uracil DNA glycosylase) mutation [Kunkel method, Proceedings of the National Academy of Sciences of the USA, vol. 82, p. 488 to 492 (1985)], a method including amber mutation using DNA polymerase and DNA ligase [Oligonucleotide-directed Dual Amber: ODA, Gene, vol. 152, p. 271 to 275 (1995), Japanese Unexamined Patent Application Publication No. 7-289262], a method of using a host which induced DNA repair system (Japanese Unexamined Patent Application Publication No. 8-70874), a method using a protein which catalyzes DNA chain exchange reaction (Japanese Unexamined Patent Application Publication No. 8-140685), a PCR method using two mutation introducing primers having restricted enzyme recognition sites (U.S. Pat. No. 5,512,463), a PCR method using a double-stranded DNA vector and two primers having inactivated drug resistant genes [Gene, vol. 103, p. 73 to 77 (1991)], and a PCR method using amber mutation [International Publication WO98/02535].

The use of a commercially available kit facilitates the introduction of site-specific mutation. Examples of the commercially available kit include Mutan (registered trademark)-G (Takara Shuzo Co., Ltd.) using the gapped duplex method, Mutan (registered trademark)-K (Takara Shuzo Co., Ltd.) using the Kunkel method, Mutan (registered trademark)-ExpressKm (Takara Shuzo Co., Ltd.) using the ODA method, and QuikChange™ Site-Directed Mutagenesis Kit (STRATAGENE) using a mutation introducing primer and DNA polymerase derived from *Pyrococcus furiosus*. Examples of the kit using the PCR method include TaKaRa LA PCR in vitro Mutagenesis Kit (Takara Shuzo Co., Ltd.) and Mutan (registered trademark)-Super Express Km (Takara Shuzo Co., Ltd.).

As described above, the present invention provides the primary structure and gene structure of a maltotriosyl transferase, and thus allows genetic engineering production of a protein having maltotriosyl transferase activity at a low cost, with high purity.

(Recombinant vector) Another aspect of the present invention relates to a recombinant vector containing the maltotriosyl transferase gene of the present invention. In the present description, the term "vector" means a nucleic acid molecule capable of transporting the nucleic acid molecule inserted therein into the target such as a cell type, and the type and form of the vector are not particularly limited. Accordingly, the vector of the present invention may be in the form of a plasmid vector, a cosmid vector, a phage vector, or a virus vector (for example, an adenovirus vector, an adeno-associated virus vector, a retrovirus vector, or a herpesvirus vector).

An appropriate vector is selected according to the intended use (cloning or protein expression), and in consideration of the type of the host cell. Specific examples of the vector include vectors in *Escherichia coli* (M13 phage or its variants, γ, phage and its variants, pBR322 and its variants (for example, pB325, pAT153, and pUC8)), vectors in yeast (for example, pYepSec1, pMFa, and pYES2), vectors in insect cells (for example, pAc and pVL), and vectors in mammalian cells (for example, pCDM8 and pMT2PC).

The recombinant vector of the present invention is preferably an expression vector. The term "expression vector" means a vector capable of introducing the nucleic acid inserted therein into the desired cell (host cell), and expressing it in the cell. The expression vector normally contains the promoter sequence necessary for the expression of the nucleic acid inserted therein, and an enhancer sequence promoting the expression. An expression vector containing a selection marker may be used. When the expression vector of this type is used, whether the expression vector has been introduced or not (and the degree of introduction) can be ascertained using the selection marker.

The insertion of the gene of the present invention into the vector, insertion of the selection marker gene (when necessary), and insertion of promoter (when necessary) may be carried out using a standard recombinant DNA technique (for example, a well-known method using a restriction enzyme and DNA ligase, see Molecular Cloning, Third Edition, 1.84, Cold Spring Harbor Laboratory Press, New York).

(Transformant) The present invention also relates to a host cell (transformant) into which the gene of the present invention has been introduced. In the transformant of the present invention, the gene of the present invention exists as a foreign molecule. The transformant of the present invention is preferably prepared by transfection or transformation using the above-described vector of the present invention. The transfection or transformation may be carried out by, for example, the calcium phosphate cosedimentation method, electroporation (Potter, H. et al., Proc. Natl. Acad. Sci. U.S.A. 81, 7161-7165 (1984)), lipofection (Feigner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73, 366-370 (1976)), Hanahan's method (Hanahan, D., J. Mol. Biol. 166, 557-580 (1983)), lithium acetate method (Schiestl, R. H. et al., Curr. Genet. 16, 339-346 (1989)), or protoplast-polyethylene glycol method (Yelton, M. M. et al., Proc. Natl. Acad. Sci. 81, 1470-1474 (1984)).

The host cell is not particularly limited as long as the maltotriosyl transferase of the present invention is expressed, and is selected from, for example, bacteria belonging to the genus *Bacillus* such as *Bacillus subtillus*, *Bacillus* likemiformis, and *Bacillus circulans*, lactic acid bacteria such as *Lac-* tococcus, *Lactobacillus, Streptococcus, Leuconostoc,* and *Bifidobacterium,* other bacteria such as *Escherichia* and *Streptomyces,* yeasts such as *Saccharomyces, Kluyveromyces, Candida, Torula,* and *Torulopsis,* and filamentous bacteria (fungi) belonging to the genus *Aspergillus,* such as *Aspergillus oryzae* and *Aspergillus niger,* and those belonging to the genus *Penicillium, Trichoderma,* and *Fusarium.*

(Method for producing maltotriosyl transferase) Yet another aspect of the present invention provides a method for producing a maltotriosyl transferase. One embodiment of the production method of the present invention includes a step of incubating a microorganism belonging to the genus *Geobacillus* and having a capability to produce the present enzyme (maltotriosyl transferase) (step (1)), and a step of collecting a maltotriosyl transferase from the culture solution and/or bacterial cells after culturing (step (2)).

The microorganism belonging to the genus *Geobacillus* in the step (1) is not particularly limited as long as it has a capacity of producing the present enzyme. For example, the above-described *Geobacillus* sp. APC9669 may be used as the microorganism. The culture method and culture conditions are not particularly limited as long as the desired enzyme is produced. More specifically, on condition that the present enzyme is produced, the culture method and conditions may be appropriately established according to the microorganism used. The culture method may be liquid culture or solid culture, and is preferably liquid culture. Taking liquid culture as an example, the culture conditions are described below.

The medium is not particularly limited as long as it is suitable for growing the microorganism used. Examples of the medium include those containing a carbon source such as glucose, sucrose, genthiobiose, soluble starch, glycerol, dextrin, molasses, or an organic acid, in addition, ammonium sulfate, ammonium carbonate, ammonium phosphate, ammonium acetate, or a nitrogen source such as peptone, yeast extract, corn steep liquor, casein hydrolysate, bran, or meat extract, in addition an inorganic salt such as a potassium salt, a magnesium salt, a sodium salt, a phosphate, a manganese salt, an iron salt, or a zinc salt. In order to accelerate the growth of the microorganism, a vitamin and an amino acid may be added to the medium. The pH of the medium is adjusted to, for example, about 3 to 10, and preferably about 7 to 8, and the incubation temperature is normally from about 10 to 80° C., preferably about 30 to 65° C. The microorganism is cultured for about 1 to 7 days, preferably for about 2 to 4 days under aerobic conditions. The culture method may be, for example, a shake culture method or an aerobic deep culture method using a jar fermenter.

After culturing under the above-described conditions, a maltotriosyl transferase is collected from the culture solution or bacterial cells (step (2)). When the enzyme is collected from the culture solution, for example, the culture supernatant is subjected to, for example, filtration or centrifugation thereby removing insoluble matter, followed by separation and purification through an appropriate combination of, for example, concentration using an ultrafiltration membrane, salting out by ammonium sulfate precipitation, dialysis, and various chromatography procedures such as ion exchange chromatography, and thus obtaining the present enzyme.

On the other hand, when the enzyme is collected from bacterial cells, the bacterial cells are crushed by, for example, pressurization or ultrasonication, and then subjected to separation and purification in the same manner as described above, and thus obtaining the present enzyme. Alternatively, the bacterial cells may be collected in advance from the culture solution by, for example, filtration or centrifugation, and then the above-described procedure (crushing of bacterial cells, separation, and purification) may be carried out.

Confirmation of expression and identification of the expression product are readily achieved using an antibody against the maltotriosyl transferase. Alternatively, the expression may be confirmed by measuring the maltotriosyl transferase activity.

According to another embodiment of the present invention, a maltotriosyl transferase is produced using the above-described transformant. In the production method according to this embodiment, firstly, the transformant is cultured under the conditions suitable for the production of the protein to be coded by the gene introduced into the transformant (step (i)). Culture conditions for transformants containing various vector hosts are known, and those skilled in the art can readily establish appropriate culture conditions. Following the culturing step, the produced protein (more specifically maltotriosyl transferase) is collected (step (ii)). The collection and subsequent purification are carried out in the same manner as in the above-described embodiment.

The degree of purification of the present enzyme is not particularly limited. In addition, the final form may be liquid or solid (including powder).

(Enzyme product) The enzyme of the present invention may be provided in the form of an enzyme product. The enzyme product may contain, in addition to the active ingredient (the enzyme of the present invention), an excipient, a buffer, a suspending agent, a stabilizer, a preservative, an antiseptic, or a normal saline solution. Examples of the excipient include starch, dextrin, maltose, trehalose, lactose, D-glucose, sorbitol, D-mannitol, white sugar, and glycerol. Examples of the buffer include phosphates, citrates, and acetates. Examples of the stabilizer include propylene glycol and ascorbic acid. Examples of the preservative include phenol, benzalkonium chloride, benzyl alcohol, chlorobutanol, and methylparaben. Examples of the antiseptic include ethanol, benzalkonium chloride, paraoxybenzoic acid, and chlorobutanol.

(Use of maltotriosyl transferase) Another aspect of the present invention is to provide a food production and processing method as a use of the maltotriosyl transferase (the present enzyme). According to the food production and processing method of the present invention, the present enzyme is acted on a food or food ingredient containing a polysaccharide and/or an oligosaccharide having $\alpha$-1,4 glucoside bonds, thereby improving the function of the food. Examples of the food include bread, rice, and rice cake. Examples of the food ingredient include various ingredients containing starch, amylose, amylopectin, and maltooligosaccharide. The purity of the ingredient is not particularly limited. The present enzyme may be acted on the ingredient mixed with other substance. Alternatively, the present enzyme may be acted on two or more ingredients at the same time.

EXAMPLES

Measurement of maltotriosyl transferase activity> The activity of the maltotriosyl transferase was measured as follows. More specifically, 0.5 mL of an enzyme solution was added to 2 mL of a 10 mmol/L MES buffer solution (pH 6.5) containing 1% maltotetraose (Hayashibara Biochemical Laboratories, Inc.), and allowed to stand at 40° C. for 60 minutes. After the standing, the mixture was heated for 5 minutes in a boiling water bath, and then cooled in running water. The amount of glucose thus produced was quantified by Glucose CII-test WAKO (Wako Pure Chemical Industries, Ltd.). Under the present conditions, the amount of the enzyme producing 1 mmol of glucose in 2.5 mL of the reaction solution for 1 minute was set at 1 unit.

<Confirmation of maltotriosyl transferase activity> The activity of the maltotriosyl transferase was confirmed as follows, together with the above-described <Measurement of maltotriosyl transferase activity>. More specifically, 15 μL of a 1.0 u/mL enzyme solution was added to 985 μL of a 5 mmol/L acetic acid buffer solution (pH 6.0) containing 10.3 mmol/L maltotetraose (Hayashibara Biochemical Laboratories, Inc.), and allowed to stand for 1, 2, or 3 hours at 50° C. After the standing, the mixture was heated in a boiling water bath for 5 minutes, and then cooled in running water. The cooled reaction solution was desalted as needed using a cationic resin and an anionic resin, and the reaction solution was analyzed by HPLC. The HPLC apparatus was "Prominence UFLC" manufactured by Shimadzu Co., Ltd., the column was "MCI GEL CK04S" manufactured by Mitsubishi Chemical Corporation, the eluent was water at a flow rate of 0.4 mL/minute, and the detection was carried out using a differential refractometer. The area percentages of the substrate and product obtained were converted to molar quantities, and the consumption rate and production rate were calculated. When a purified maltotriosyl transferase was analyzed, for example, the ratio of the production rate was, for example, heptasaccharide:trisaccharide=about 92:about 8.

1. Production and purification of maltotriosyl transferase derived from *Geobacillus* sp. APC9669 *Geobacillus* sp. APC9669 was cultured under shaking at 45° C. for 2 days using the liquid medium having the composition shown in Table 1. The culture supernatant thus obtained was concentrated by five folds using a UF membrane (AIP-1013D, Asahi Kasei Corporation), and then ammonium sulfate was added to make a 50% saturated solution. The precipitate fraction was redissolved in a 20 mmol/L tris-hydrochloride buffer (pH 8.0) containing 5 mmol/L calcium chloride, and then ammonium sulfate was added to give a final concentration of 0.5 mol/L. After removing the precipitate thus formed by centrifugation, the solution was passed through HiLoad 26/10 Phenyl Sepharose HP column (GE Healthcare) which had been equilibrated with a 20 mmol/L tris-hydrochloride buffer (pH 8.0) containing 0.5 mol/L ammonium sulfate and 5 mmol/L calcium chloride, and the adsorbed maltotriosyl transferase protein was eluted by ammonium sulfate linear concentration gradient from 0.5 mol/L to 0 mol/L

TABLE 1

| Maltotriosyl transferase producing medium | |
|---|---|
| | (w/v) |
| Yeast extract | 1.5% |
| Soybean peptone | 0.5% |
| Sodium chloride | 0.5% |
| Soluble starch | 0.4% |

The collected maltotriosyl transferase active fraction was concentrated using a UF membrane, and the buffer was replaced with a 20 mmol/L tris-hydrochloride buffer (pH 8.0) containing 5 mmol/L calcium chloride. The sample in the replaced buffer was passed through HiLoad 26/10 Q Sepharose HP column (GE Healthcare) which had been equilibrated with a 20 mmol/L tris-hydrochloride buffer (pH 8.0) containing 5 mmol/L calcium chloride, and the adsorbed maltotriosyl transferase protein was eluted by NaCl linear concentration gradient from 0 mol/L to 1 mol/L.

Furthermore, the collected maltotriosyl transferase active fraction was concentrated using a UF membrane, and then the buffer was replaced with a 50 mM phosphate buffer solution (pH 7.2) containing 0.15 M NaCl. The solution was passed through HiLoad 26/60 Superdex 200 pg column (GE Healthcare) which had been equilibrated with a 50 mM phosphate buffer solution (pH 7.2) containing 0.15 M NaCl, and eluted by the buffer solution. The maltotriosyl transferase active fraction was collected, and desalted and concentrated using an ultrafiltration membrane, and thus obtaining a purified enzyme preparation. The purified enzyme was subjected to the following evaluation of various properties.

Figure 5:
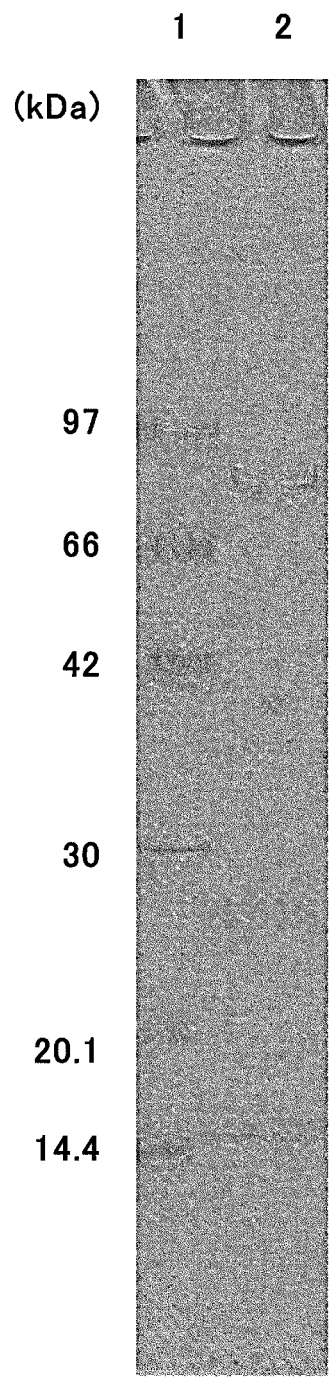
FIG. 5 shows the result of SDS-PAGE analysis on the maltotriosyl transferase. Lane 1: molecular weight marker; Lane 2: maltotriosyl transferase.

The results of purification in the respective steps are shown in Table 2. The specific activity in the final stage was about 41 times that of the crude enzyme. FIG. 5 shows the result of SDS-PAGE (CBB staining) in a 10-20% gradient gel carried out on the samples in the respective steps of the purification process. The result indicates that the purified enzyme preparation (Lane 2) is a single protein in the SDS-PAGE.

TABLE 2

| | Total amount of protein (mg) | Total activity (U) | Specific activity (u/mg) | Recovery rate (%) |
|---|---|---|---|---|
| Concentrate | 42 | 300 | 3.9 | 100 |
| Ammonium sulfate fraction | 8.5 | 220 | 22.9 | 73 |
| Phenyl HP | 0.50 | 58 | 100 | 19 |
| Q HP | 0.37 | 53 | 139 | 18 |
| Superdex 200 | 0.12 | 19 | 158 | 6.3 |

2. Properties of maltotriosyl transferase (1) Optimum reaction temperature In accordance with the above-described maltotriosyl transferase activity measurement method, reaction was carried out at reaction temperatures of 30° C., 40° C., 45° C., 50° C., 55° C., 60° C., 65° C., 70° C., and 75° C. The results were expressed as relative activity, taking the value at the temperature at which the highest activity was exhibited as 100%. The optimum reaction temperature was in the vicinity of 50° C. (FIG. 1).

Figure 2:
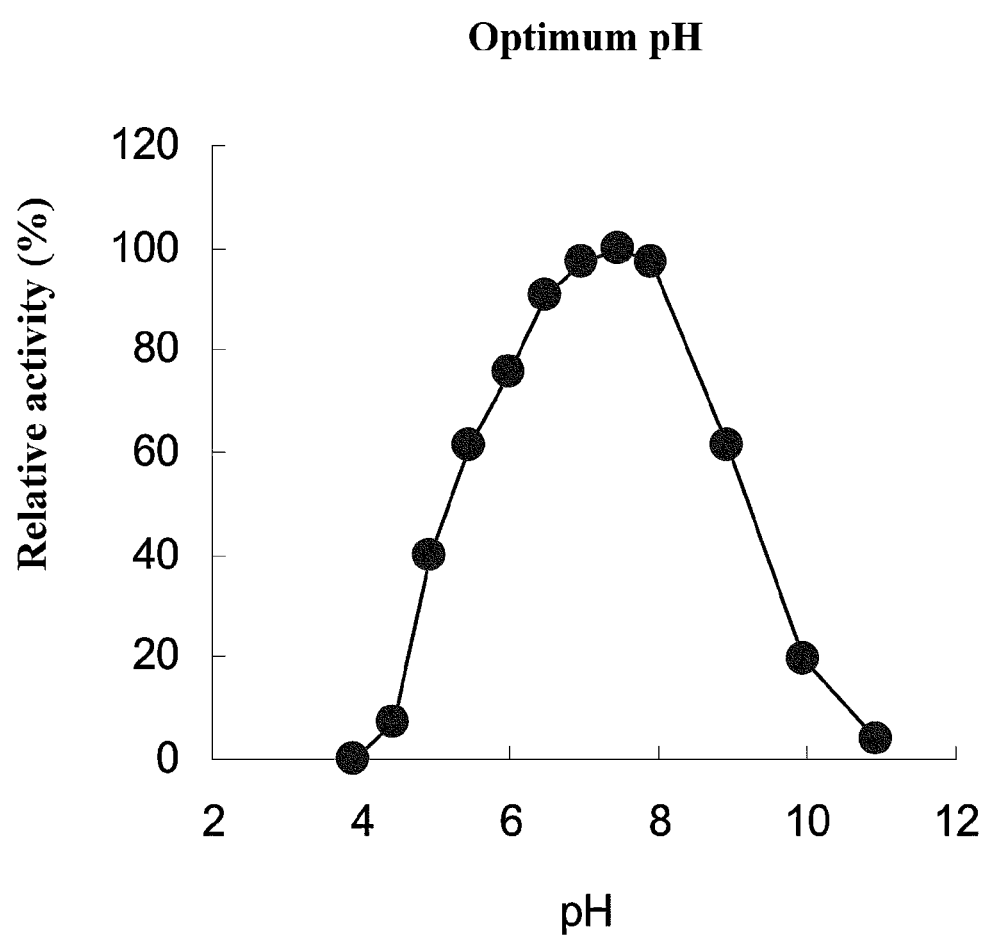
FIG. 2 is a graph showing the optimum pH for the maltotriosyl transferase derived from *Geobacillus* sp. APC9669.

(2) Optimum reaction pH In accordance with the above-described maltotriosyl transferase activity measurement method, the measurement was carried out under reaction conditions at 40° C. for 60 minutes in buffer solutions (universal buffer solutions at pH 4.0, pH 4.5, pH 5.0, pH 5.5, pH 6.0, pH 6.5, pH 7.0, pH 7.5, pH 8.0, pH 9.0, pH 10.0, and pH 11.0). The results were expressed as relative activity, taking the value at the pH at which the highest activity was exhibited as 100%. The optimum reaction pH was in the vicinity of about 7.5 (FIG. 2).

Figure 3:
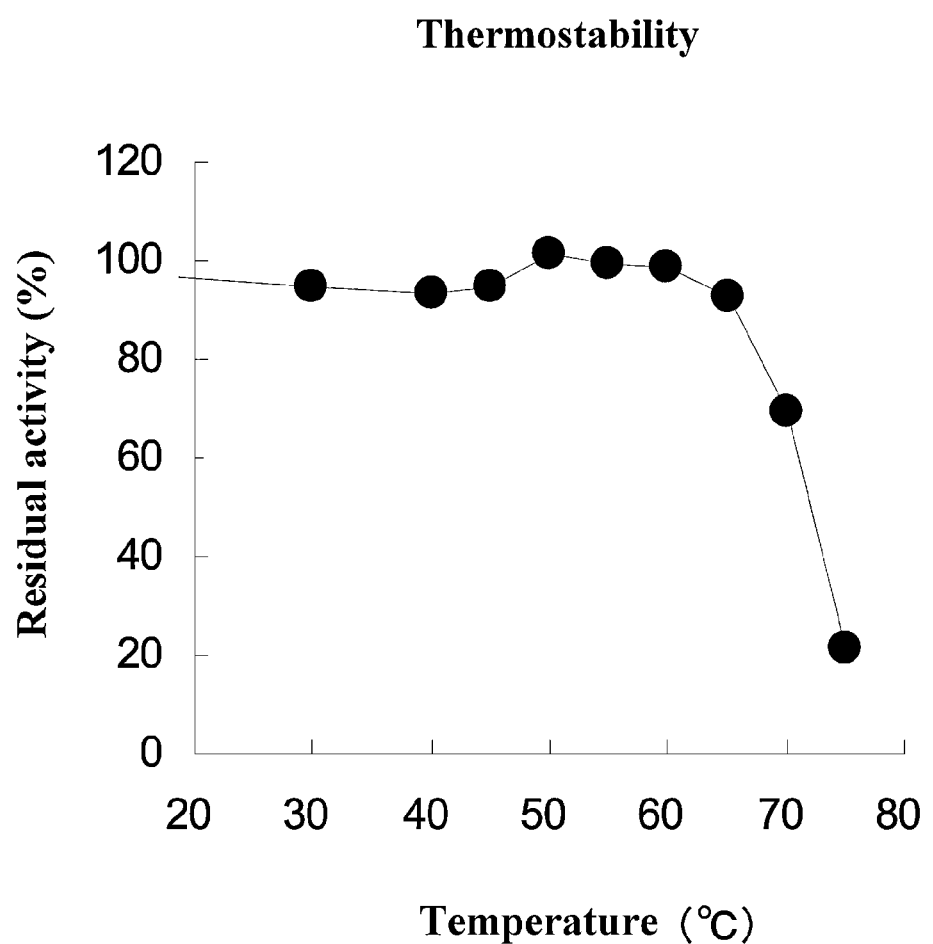
FIG. 3 is a graph showing the thermostability of the maltotriosyl transferase derived from *Geobacillus* sp. APC9669.

(3) Thermostability A 6 u/mL enzyme solution was heat treated for 30 minutes at 30° C., 40° C., 45° C., 50° C., 55° C., 60° C., 65° C., 70° C., or 75° C. in a 10 mmol/L MES buffer solution (pH 6.5), and then residual activity was measured in accordance with the above-described maltotriosyl transferase activity measurement method. The results were expressed as residual activity, taking the activity of the sample unheated as 100%. After heat treatment at 65° C. for 30 minutes, the residual activity was 90% or more, and the activity was stable up to 65° C. (FIG. 3).

Figure 4:
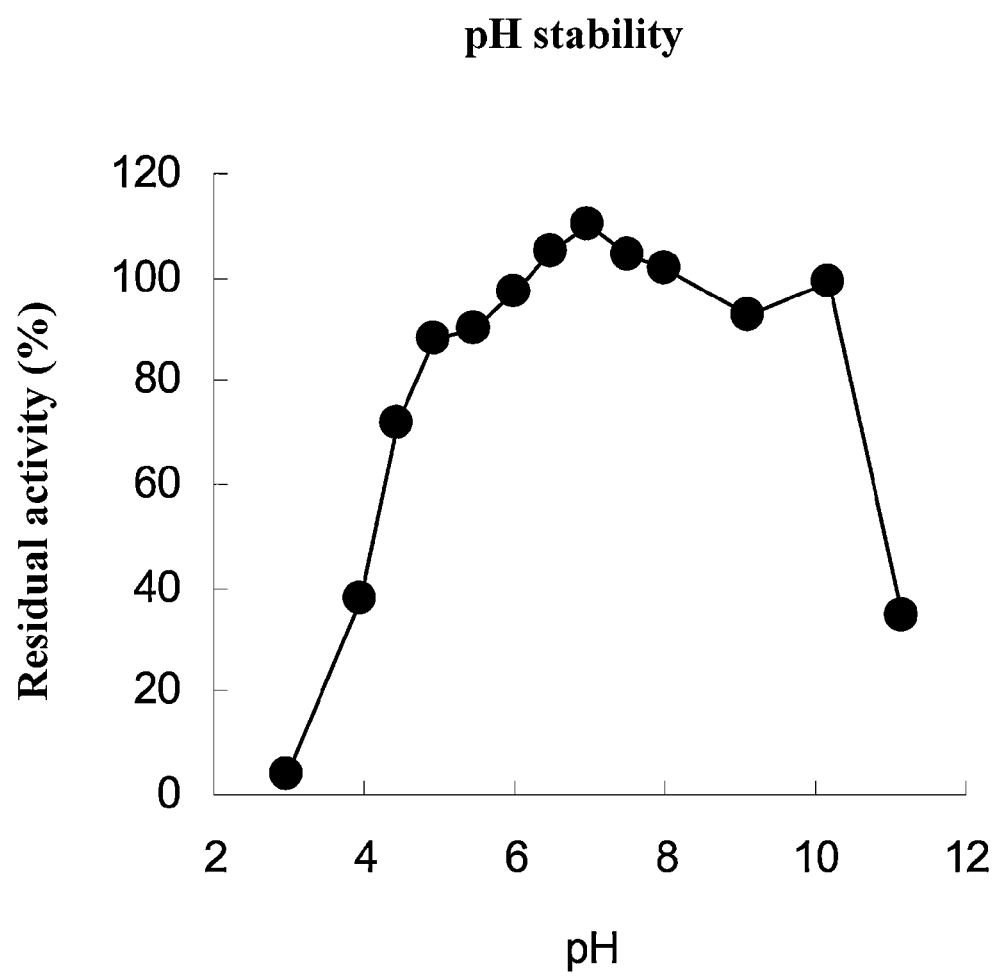
FIG. 4 is a graph showing the pH stability of the maltotriosyl transferase derived from *Geobacillus* sp. APC9669.

(4) pH stability A 6 u/mL enzyme solution was treated at 40° C. for 30 minutes in a buffer solution (universal buffer solution at pH 3.0, pH 4.0, pH 4.5, pH 5.0, pH 5.5, pH 6.0, pH 6.5, pH 7.0, pH 7.5, pH 8.0, pH 9.0, pH 10.0, or pH 11.0), and then the activity was measured in accordance with the above-described maltotriosyl transferase activity measurement method. In the range from pH 5.0 to pH 10.0, the residual activity was 85% or more, and the activity was stable in the range from pH 5.0 to pH 10.0 (FIG. 4).

(5) Molecular weight measurement by SDS-PAGE SDS-PAGE was carried out in accordance with by the method of Laemmli et al. The molecular weight marker used herein was Low Molecular Weight Calibration Kit for Electrophoresis (GE Healthcare), which contained Phosphorylase b (97,000 Da), Albumin (66,000 Da), Ovalbumin (45,000 Da), Carbonic anhydrase (30,000 Da), Trypsin inhibitor (20,100 Da), or α-Lactalbumin (14,400 Da) as the standard protein. Electrophoresis was carried out at 20 mA/gel for about 80 minutes using a gradient gel at a gel concentration of 10-20% (Wako Pure Chemical Industries, Ltd.), and the molecular weight was determined; the molecular weight was about 83 kDa (FIG. 5).

(6) Isoelectric point The isoelectric point of the present enzyme was about 4.5, as measured by isoelectric focusing (600V, 4° C., 48 hours) using Ampholine.

(7) Substrate specificity The maltotriosyl transferase activity for different substrates was tested. a) Substrate specificity to maltooligosaccharide Substrate specificity to maltooligosaccharides was tested by the following method. The enzyme was added to 10 mmol/L maltooligosaccharides so as to give a concentration of 0.002 u/mL, and allowed to stand at 50° C. for 1, 2, or 3 hours. After the standing, the mixture was heated in a boiling water bath for 5 minutes, and then cooled in running water. The cooled reaction solution was desalted as needed using a cationic resin and an anionic resin, and the reaction solution was analyzed by HPLC. The HPLC apparatus was "Prominence UFLC" manufactured by Shimadzu Co., Ltd., the column was "MCI GEL CK04S" manufactured by Mitsubishi Chemical Corporation, the eluent was water at a flow rate of 0.4 mL/minute, and the detection used a differential refractometer. The area percentages of the substrate and product obtained were converted to molar quantities, and the consumption rate and production rate were calculated. The reaction rates for the respective maltooligosaccharides were calculated as follows. The rate for maltotetraose was the sum of the heptasaccharide and trisaccharide production rates. The rate for maltopentaose was the sum of the octasaccharide and trisaccharide production rates. The rate for maltohexaose was calculated by halving the difference between the trisaccharide and nonasaccharide production rates, and then adding the value to the nonasaccharide production rate.

TABLE 3

| Substrate | Relative rate (%) |
|---|---|
| Maltose | 0 |
| Maltotriose | 0 |
| Maltotetraose | 83 |
| Maltopentaose | 100 |
| Maltohexaose | 89 |

No reaction product was observed for maltose and maltotriose. High activity was exhibited for maltotetraose, maltopentaose, and maltohexaose.

b) Substrate specificity to polysaccharides Substrate specificity to cyclodextrin, soluble starch, amylose, and amylopectin was tested by the following method. The enzyme was added to 10 mmol/L maltooligosaccharides so as to give a concentration of 0.002 u/mL, and allowed to stand at 50° C. for 1, 2, or 3 hours. After the standing, the mixture was heated in a boiling water bath for 5 minutes, and then cooled in running water. To 200 μL of the solution, Rhizopus-derived glucoamylase (Wako Pure Chemical Industries, Ltd.) was added in a concentration of 0.03 mg in 1.0 unit, and allowed to stand at 50° C. overnight. After the standing, the mixture was heated in a boiling water bath for 5 minutes, and then cooled in running water. The cooled reaction solution was desalted as needed using a cationic resin and an anionic resin, and the reaction solution was analyzed by HPLC. The HPLC apparatus was "Prominence UFLC" manufactured by Shimadzu Co., Ltd., the column was "MCI GEL CK04S" manufactured by Mitsubishi Chemical Corporation, the eluent was water at a flow rate of 0.4 mL/minute, and the detection used a differential refractometer. When the sample treated with the enzyme (maltotriosyl transferase) showed a time-dependent increase of the peak of trisaccharide or higher saccharide in comparison with the untreated sample, the reaction product was judged as present (+), while no increase was observed, the reaction product was judged as absent (−).

TABLE 4

| Substrate | Presence or absence of product |
|---|---|
| α-cyclodextrin | − |
| β-cyclodextrin | − |
| γ-cyclodextrin | − |
| Amylose | + |
| Amylopectin | + |
| Soluble starch | + |

For cyclodextrin, no reaction product was observed. For soluble starch, amylose, and amylopectin, time-dependent increases were found in the peaks of trisaccharide or higher saccharide. These polysaccharides were found to serve as substrates. The fact that glucoamylase hydrolyzes α-1,4 and α-1,6 bonds indicates that transglycosylation products were formed also for other binding modes.

(8) Influence of substrate concentration on enzyme reaction product The influence of the substrate concentration on the enzyme reaction product was studied using maltotetraose as substrate. The enzyme was added to 0.67, 1.0, 3.0, 10, 30, or 70% (w/v) maltotetraose in such a manner that the maltotetraose residue is 85% or more after reaction for 3 hours, and allowed to stand at 50° C. for 1, 2, or 3 hours. After the standing, the mixture was heated in a boiling water for 5 minutes, and cooled in running water. The cooled reaction solution was desalted as needed using a cationic resin and an anionic resin, and the reaction solution was analyzed using HPLC. The HPLC apparatus was "Prominence UFLC" manufactured by Shimadzu Co., Ltd., the column was "MCI GEL CK04S" manufactured by Mitsubishi Chemical Corporation, the eluent was water at a flow rate of 0.4 mL/minute, and the detection used a differential refractometer. The area percentages of the substrate and product obtained were converted to molar quantities, and the production rate was calculated. The results indicate that the transglucosylation was 90% or more under all the substrate concentration conditions (from 0.67 to 70% (w/v)).

TABLE 5

| | Reaction production rate (molar ratio) | |
|---|---|---|
| Substrate concentration (% (w/v)) | Transfer product (heptasaccharide) | Decomposition product (trisaccharide) |
| 0.67 | 92% | 8% |
| 1.0 | 96% | 4% |
| 3.0 | 100% | 0% |
| 10 | 100% | 0% |
| 30 | 100% | 0% |
| 70 | 100% | 0% |

Figure 6:
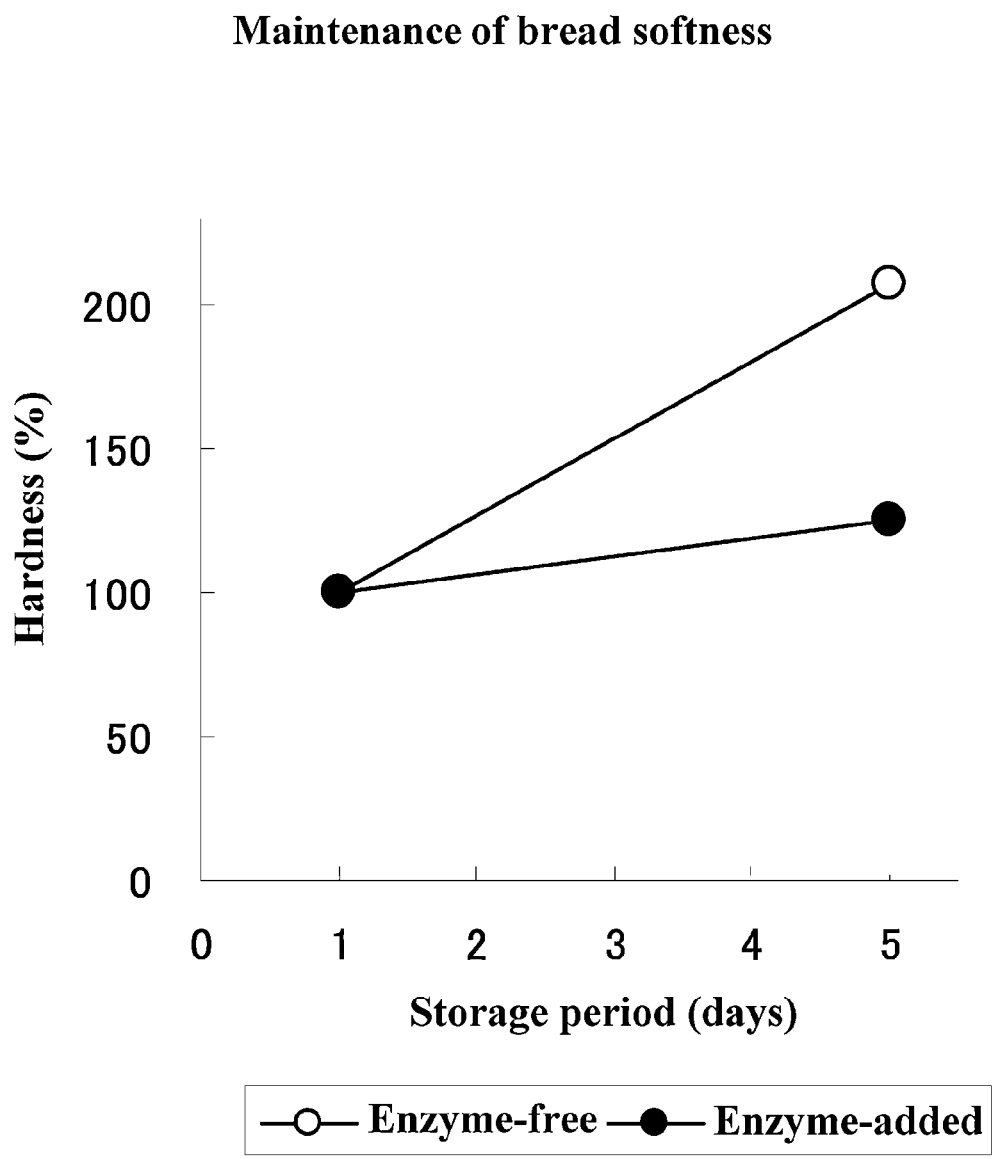
FIG. 6 shows the results of bread softness retention test.

3. Bread baking The maltotriosyl transferase was added to bread dough, and baked into bread. Basic ingredients of English loaf (strong flour 260 g; sugar 13 g; salt 5.2 g; shortening 10.4 g; L-ascorbic acid 0.013 g; cold water 192 g; and dry yeast 3.1 g) or the mixture of the basic ingredients and 120 u of the maltotriosyl transferase was charged into National Automatic Home Bakery SD-BT150 (Panasonic Corporation). After baking, the bread was allowed to cool at 26° C. for 1 hour, subsequently the bread was placed in a plastic bag so as to prevent moisture evaporation, and stored at 26° C. After storage for 1 or 5 days, the bread was sliced into 2 cm thick pieces, and the central portion of the bread was cut into a column having a diameter of 47 mm. The hardness of the bread was determined by measuring the maximum load when the bread was compressed by 1.5 cm at a compression speed of 2 mm/minute, using FUDOH rheometer NRM-2002J (Sun Scientific Co., Ltd., Rheotech). The results are shown in FIG. 6. The hardness of the bread stored for five days was compared between the enzyme-containing and enzyme-free samples, taking the hardness of the bread after storage for one day as 100%. The hardness of the enzyme-containing sample was 125%, indicating that hardening of the bread was suppressed and softness was maintained in comparison with those of the enzyme-free sample (hardness: 207%).

4. Rice cooking 75 g of rice was washed with water, to which 150 mL of water was added alone or together with 40 u of the maltotriosyl transferase, the mixture was allowed to stand for 2 hours at room temperature, and then cooked by an ordinary procedure to obtain cooked rice. The cooked rice was stored at 4° C. for 7 days. The degree of gelatinization before and after storage was measured by the BAP method. The degree of gelatinization of the enzyme-containing sample was 96.6% immediately after rice cooking, and 69.5% after 7 days as measured by the BAP method (Table 6). On the other hand, the degree of gelatinization of the enzyme-free sample was 95.3% immediately after rice cooking, and 59.7% after 7 days. In the enzyme-containing sample, deterioration of the degree of gelatinization was suppressed, or retrogradation of starch was suppressed.

TABLE 6

|  | Degree of gelatinization | |
| --- | --- | --- |
|  | After 1 day | After 7 days |
| Enzyme-containing sample | 96.6% | 69.5% |
| Enzyme-free sample | 95.3% | 59.7% |

5. Production of rice cake 200 g of rice powder was mixed with 165 g of water, and steamed with water vapor for 15 minutes. Subsequently, the steamed powder was stirred in a mixer (Kitchen Aid KSM5, FMI Corporation). When the temperature of the dough reached about 65° C., 30 u of the maltotriosyl transferase was added to and mixed to make an enzyme-containing sample. The sample was molded in a plastic petri dish, allowed to cool, and stored at 15° C. After storage for 24 hours, the rice cake was sliced into 10 mm thick pieces, and the central portion of the rice cake was cut into a column having a diameter of 25 mm. The hardness of the rice cake was determined by measuring the maximum load when the rice cake was compressed by 5 mm at a compression speed of 2 mm/minute, using FUDOH rheometer NRM-2002J (Sun Scientific Co., Ltd., Rheotech). The hardness of the rice cake was compared, taking the hardness of the enzyme-free rice cake after storage for 24 hours as 100%. In addition, stickiness of the rice cake was also tested. The hardness of the enzyme-containing sample was 35%, indicating that hardening of the rice cake was suppressed, and softness was maintained (Table 7). In addition, the rice cake had no stickiness.

TABLE 7

|  | Hardness | Stickiness |
| --- | --- | --- |
| Enzyme-containing sample | 35% | None |
| Enzyme-free sample | 100% | None |

6. Acquisition of gene fragment coding maltotriosyl transferase derived from *Geobacillus* sp. APC9669 (a) Isolation of chromosomal DNA A chromosomal DNA was prepared from the bacterial cells of *Geobacillus* sp. APC9669 by the Saito and Miura's method (Non-Patent Document 5).

(b) Determination of partial amino acid sequence The purified sample of the maltotriosyl transferase obtained in 1. was subjected to the amino acid sequence analysis, and the N-terminal 10-residue amino acid sequence (SEQ ID NO: 1) and internal peptide amino acid sequence (SEQ ID NOs: 2 and 3) were determined. (c) Preparation of DNA probe by PCR Two mixed oligonucleotides (SEQ ID NOs: 4 and 5) were synthesized based on the N-terminal amino acid sequence and internal amino acid sequence, and used as PCR primers. Using these primers, PCR reaction was carried out under the following conditions, wherein the template was the chromosomal DNA of *Geobacillus* sp. APC9669. <PCR reaction solution>

10×PCR reaction buffer solution (Takara Bio Inc.) 5.0 μl dNTP mixed solution (2.5 mM, Takara Bio Inc.) 8.0 μl 25 mM MgCl$_2$ 5.0 μl 50 μM sense primer 0.5 μl 50 μM antisense primer 0.5 μl Distilled water 29.5 μl Chromosomal DNA solution (100 μg/ml) 1.0 μl LA Taq DNA polymerase (Takara Bio Inc.) 0.5 μl PCR reaction conditions> Stage 1: denaturation (95° C., 5 minutes) 1 cycle Stage 2: denaturation (95° C., 1 minute) 30 cycles Annealing (50° C., 1 minute) Extension (72° C., 1 minute) Stage 3: extention (72° C., 10 minutes) 1 cycle About 1.1 kb of DNA fragment thus obtained was cloned into pGEM-Teasy (Promega K.K.), and then the base sequence was confirmed; the base sequence coding the above-described partial amino acid sequence was found immediately after the sense primer and immediately before the antisense primer. This DNA fragment was used as the DNA probe for cloning the full length gene.

(d) Construction of gene library As a result of the southern hybridization analysis of the chromosomal DNA of *Geobacillus* sp. APC9669, a single band of about 5.2 kb hybridizing with the probe DNA was found in the EcoRI digestion product. In order to clone the EcoRI DNA fragment of about 5.2 kb, a gene library was constructed as follows. The chromosomal DNA prepared in the above-described (a) was subjected to EcoRI treatment. 50 μg of the chromosomal DNA, 40 μl of 10×H buffer solution, 342.0 μl of distilled water, and 8.0 μl of EcoRI were mixed, and treated at 37° C. for 15 hours. The digestion product thus obtained was ligated into the EcoRI-treated pBluescript II KS+ vector (Stratagene), and thus obtaining a gene library.

(e) Screening of gene library The DNA fragment of 1.1 kb obtained in the above-described (c) was labeled using DIG-High Prime (Roche). Using this as DNA probe, the gene library obtained in (d) was screened by colony hybridization. A pBlue-SAS plasmid was obtained from the positive colony thus obtained.

(f) Determination of base sequence The base sequence of the pBlue-SAS plasmid was determined by an ordinary procedure. The base sequence (2304 bp) coding the maltotriosyl transferase derived from *Geobacillus* sp. APC9669 is set forth in SEQ ID NO: 6. In addition, the amino acid sequence (767 amino acids) coded by SEQ ID NO: 6 is set forth in SEQ ID NO: 7. In the amino acid sequence, the N-terminal region amino acid sequence (SEQ ID NO: 1) determined in (b) and the internal amino acid sequences (SEQ ID NOs: 2 and 3) were found. The amino acid sequence excluding the signal peptide from the amino acid sequence set forth in SEQ ID NO: 7 is set forth in SEQ ID NO: 8.

7. Expression of maltotriosyl transferase derived from *Geobacillus* sp. APC9669 in *Escherichia coli* (a) Construction of plasmid expressing maltotriosyl transferase in *Escherichia coli* Two oligonucleotides (SEQ ID NOs: 9 and 10) were synthesized based on the DNA sequences coding the N-terminal region amino acid sequence and C-terminal region amino acid sequence, and used as PCR primers. The sense primer contained the SacI restriction enzyme recognition site, and the antisense primer contained the XbaI restriction enzyme recognition site. Using these primers and the chromosomal DNA having a maltotriosyl transferase gene as templates, PCR reaction was carried out under the following conditions. <PCR reaction solution>

10×PCR reaction buffer solution (TOYOBO) 5.0 µl dNTP mixed solution (respectively 2.5 mM, TOYOBO) 5.0 µl 10 µM sense primer 1.5 µl 10 µM antisense primer 1.5 µl 25 mM MgSO$_4$ 2.0 µl Distilled water 33.0 µl Chromosomal DNA solution (200 µg/ml) 1.0 µl KOD-Plus-DNA polymerase (TOYOBO) 1.0 µl <PCR reaction conditions> Stage 1: denaturation (94° C., 2 minutes) 1 cycle Stage 2: denaturation (94° C., 15 seconds) 30 cycles Annealing (50° C., 30 seconds) Extension (68° C., 2 minutes 30 seconds)

The PCR product thus obtained was confirmed by electrophoresis, and desalted by ethanol precipitation (84 µl). Subsequently, 10 µl of a 10×M buffer solution, 3 µl of SacI, and 3 µl of xbaI were added, and subjected to enzyme treatment at 37° C. for 15 hours. The solution treated with the restriction enzyme was confirmed by electrophoresis, purified by NucleoSpin Extract II (Nippon Genetics Co., Ltd.), and then ligated into pColdII DNA vector (Takara Bio Inc.), which had been treated with SacI and XbaI, and thus obtaining a expression plasmid pColdII-SAS.

(b) Expression of maltotriosyl transferase in *Escherichia coli* The expression plasmid pColdII-SAS was introduced into *Escherichia coli* JM109 Competent Cells (Takara Bio Inc.). From the transformants obtained as ampicillin-resistant strains, the strains having pColdII-SAS into which the intended maltotriosyl transferase gene had been inserted were selected by colony PCR. In addition, the transformant of *Escherichia coli* JM109 having the expression vector pColdII DNA was also obtained as control. These transformants were inoculated in 1 ml of the LB medium containing 100 µg/ml of ampicillin, and cultured until O.D 600 reached 0.4-1.0 at 37° C., 170 rpm (preculture). Subsequently, 300 µl of the preculture solution was inoculated in 9 ml of the LB medium containing 100 µg/ml of ampicillin, and cultured until O.D 600 reached 0.4-1.0 at 37° C., 170 rpm. After the standing at 15° C. for 30 minutes, 9 µl of 0.1 M IPTG was added, cultured at 15° C., 160 rpm for 24 hours (main culture), and the bacterial cells were collected. The bacterial cells were suspended in 1.0 ml of 100 mM Tris-HCl buffer (pH 6.5), 0.50 g of glass beads having a diameter of 0.1 mm was added, and the bacterial cells were crushed using Multi-Beads Shocker (Yasui Kikai Corporation). The crushing was achieved by repeating a cycle of 120 seconds on and 60 seconds of 3.75 times. The cell free-extract thus obtained was subjected to centrifugation, and thus obtaining a soluble component.

Figure 7:
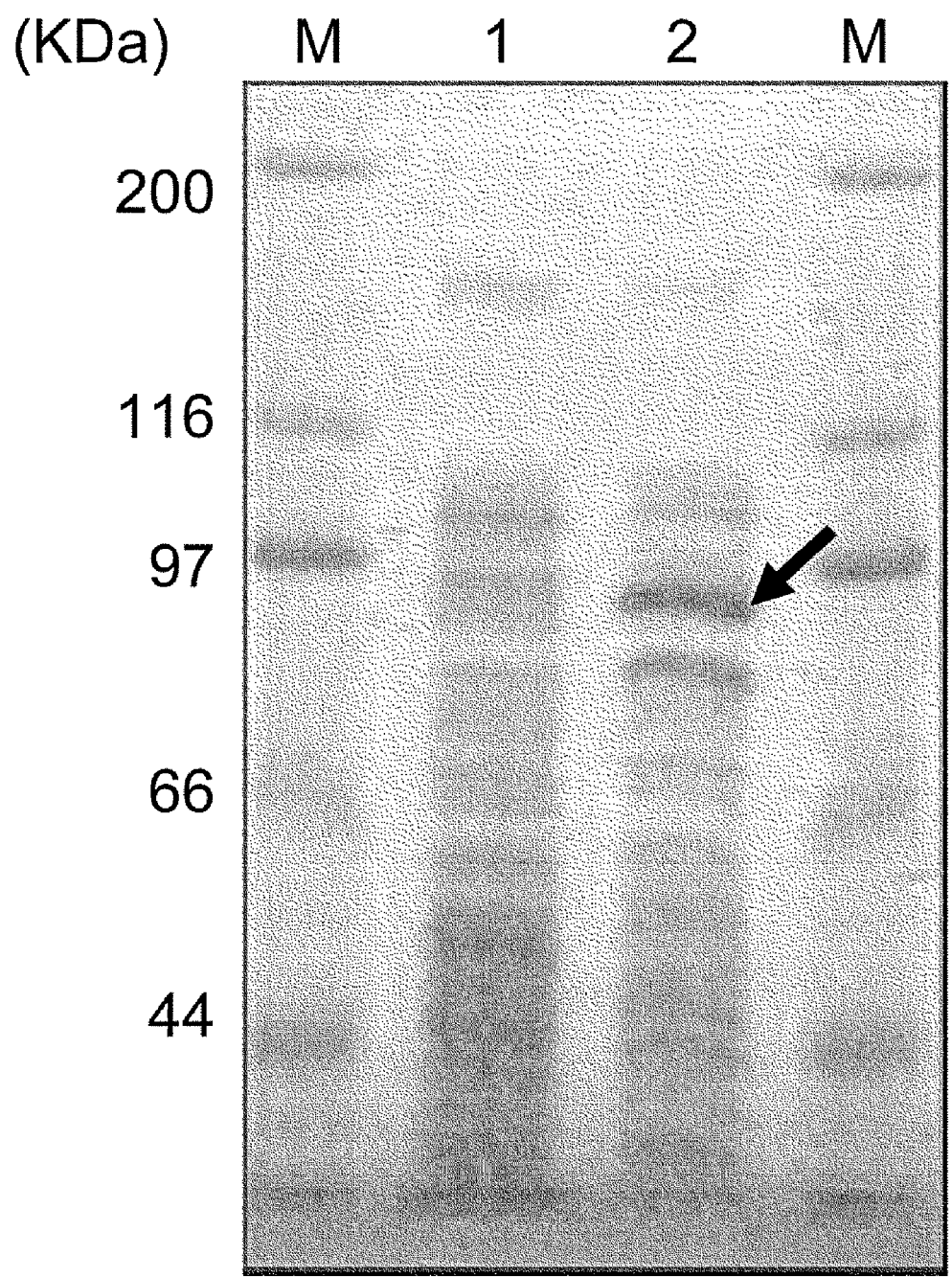
FIG. 7 shows the results of SDS-PAGE on the centrifugation supernatants of cell fragments from an *Escherichia coli* transformant. Lane M: molecular weight marker; Lane 1: centrifugation supernatant of cell fragments from *E. coli* vector transformant; Lane 2: maltotriosyl transferase.

(c) Confirmation of maltotriosyl transferase expression The soluble component thus obtained was subjected to SDS-PAGE. The electrophoretic apparatus was PhastSystem (GE Healthcare), and the separating gel was PhastGel Homogeneous 7.5 (GE Healthcare). As a result of this, as shown in FIG. 7, pColdII-SAS showed significant production of a protein which appears to be a maltotriosyl transferase in the vicinity of 83 kDa. The pColdII DNA as control showed no corresponding protein production, so that the protein was considered to be caused by the introduction of the maltotriosyl transferase gene (FIG. 7).

The same samples were measured for the activity in the same manner as the above-described maltotriosyl transferase activity measurement method. The results are shown in Table 8.

TABLE 8

|  | Activity (U/ml) | Protein (mg/ml) | Specific activity (U/mg) |
|---|---|---|---|
| pColdII-SAS | 44.3 | 0.515 | 86.1 |
| pColdII | 0.02 | 0.875 | 0.02 |

Maltotriosyl transferase activity was apparently detected in comparison with the control, and thus the expression of the intended maltotriosyl transferase was confirmed.

INDUSTRIAL APPLICABILITY

The maltotriosyl transferase of the present invention exhibits marked heat resistance, and thus is suitable for applications involving reactions at high temperatures. The use of the maltotriosyl transferase of the present invention allows enzyme reaction in high temperature environments where the risk of contamination is low. In addition, when the maltotriosyl transferase is acted on a starch-containing food, retrogradation of starch is suppressed. Accordingly, the maltotriosyl transferase of the present invention is particularly useful in food processing.

The present invention will not be limited to the description of the embodiments and examples of the present invention. Various modifications readily made by those skilled in the art are also included in the present invention, without departing from the scope of claims.

The contents of the articles, unexamined patent publications, and patent applications specified herein are hereby incorporated herein by reference. Sequence list free text SEQ ID NOs: 4, 5, 9, and 10: explanation of artificial sequence: primer

The invention claimed is:

1. An isolated maltotriosyl transferase comprising the amino acid sequence set forth in SEQ ID NO: 8.

2. The isolated maltotriosyl transferase according to claim 1, wherein the isolated maltotriosyl transferase is isolated from *Geobacillus* sp. APC9669 having deposit accession number NITE BP-770.

3. An enzyme product comprising the isolated maltotriosyl transferase of claim 1 as an active ingredient.

4. A food or food ingredient comprising the isolated maltotriosyl transferase of claim 1.

5. The isolated maltotriosyl transferase according to claim 1, wherein the isolated maltotriosyl transferase is encoded by the nucleic acid sequence set forth in SEQ ID NO: 6.

6. An enzyme product comprising the isolated maltotriosyl transferase of claim 5 as an active ingredient.

7. A method for processing a food containing a polysaccharide or oligosaccharide having α-1,4 glucoside bonds, the method comprising a step of adding the isolated maltotriosyl transferase of claim 1 to the food.

8. The method of claim 7, wherein the food containing a polysaccharide or oligosaccharide having α-1,4 glucoside bonds is selected from the group consisting of bread, rice, and rice cake.

* * * * *

SEQUENCE LISTING

<160> NUMBER OF SEQ ID NOS: 10

<210> SEQ ID NO 1
<211> LENGTH: 10
<212> TYPE: PRT

-continued

```
<213> ORGANISM: Geobacillus sp.

<400> SEQUENCE: 1

Thr Thr Ser Thr Gly Ala Leu Gly Pro Val
1               5                   10

<210> SEQ ID NO 2
<211> LENGTH: 6
<212> TYPE: PRT
<213> ORGANISM: Geobacillus sp.

<400> SEQUENCE: 2

His Phe Gly Thr Met Lys
1               5

<210> SEQ ID NO 3
<211> LENGTH: 6
<212> TYPE: PRT
<213> ORGANISM: Geobacillus sp.

<400> SEQUENCE: 3

Arg Gln Phe Tyr Asp Lys
1               5

<210> SEQ ID NO 4
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: y is c or t
<220> FEATURE:
<221> NAME/KEY: misc_feature
<222> LOCATION: (6)..(6)
<223> OTHER INFORMATION: y is c or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: r is a or g

<400> SEQUENCE: 4
cayttyggna cnatgaar                                              18

<210> SEQ ID NO 5
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: y is c or t
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (7)..(7)
<223> OTHER INFORMATION: r is a or g
```

```
<220> FEATURE:
<221> NAME/KEY: misc_feature
<222> LOCATION: (10)..(10)
<223> OTHER INFORMATION: r is a or g
<220> FEATURE:
<221> NAME/KEY: misc_feature
<222> LOCATION: (13)..(13)
<223> OTHER INFORMATION: y is c or t
<220> FEATURE:
<221> NAME/KEY: misc_feature
<222> LOCATION: (16)..(16)
<223> OTHER INFORMATION: y is c or t

<400> SEQUENCE: 5
yttrtcrtar aaytgyct                                                 18

<210> SEQ ID NO 6
<211> LENGTH: 2304
<212> TYPE: DNA
<213> ORGANISM: Geobacillus sp.

<400> SEQUENCE: 6
atgtggaagg ttccaaaatt cattaaacaa tcatatctcg ttttcttct tgctctattg      60
ctctattctt catttggttt ttcgttttcc aggactgagg cgactacatc tacaggagct    120
ttaggaccag ttaccccgaa agacacaata tatcagatcg tgacggaccg tttttttgat    180
ggcgacccat caaataacaa gcctcctggt tttgatccta ccctgtttga tgatccggac    240
ggcaataacc aggggaacgg aaaagattta agttgtatc aaggcggtga tttccaagga    300
atcatagata aaattcctta tttaaaaaat atggggataa ctgccgtttg atttccgct    360
ccttatgaaa atagggacac tgtgatagaa gattatcaat cagatggaag tattaatcgt    420
tggaccagtt ccacggtta ccatgcaaga aattattttg caactaacaa acattttggt    480
actatgaaag atttattag actacgcgat gctttgcatc aaaatggaat taaactagtg    540
atagattttg tatccaatca ttcgagtcgt tggcaaaacc cgacattgaa ttttgcgcct    600
gaagatggta aattatatga acctgacaag gatgcgaatg caattacgt atttgatgct    660
aatggagagc ctgcggatta caacggtgat ggaaaagttg agaatctcct ggcggatcca    720
cataacgacg tgaatggttt tttccatggt ctgggtgacc ggggcaacga tacttctcgt    780
tttggctacc gttacaaaga tctaggttct tggctgatt attctcagga aaatgcacta    840
gtggttgaac atttggagaa agcagctaaa ttttggaaat caaaagggat cgatggtttt    900
cgacatgatg ccactttgca tatgaatcct gcatttgtga agggatttaa agatgcaatt    960
gattcagatg caggtggccc ggttacccat tttggtgaat ttttcattgg aagaccggat   1020
cccaagtatg atgagtaccg gacatttcct gaacgaacag gagtcaacaa cttggatttt   1080
gaatatttcc gtgcggccac aaacgcattt gggaactttt ctgaaacgat gagttccttt   1140
ggtgatatga tgatcaagac aagtaatgat tacatttatg aaaatcaaac agttactttc   1200
ttggataatc atgatgtaac aagatttcgc tatattcaac caaacgataa accttatcat   1260
gcagctctcg ctgtcttgat gacatcacgt gggattccta acatttatta cggaacagag   1320
caatatctga tgccgtcaga ctcaagtgac attgcgggtc ggatgtttat gcagacttct   1380
actaacttcg atgaaaatac cactgcatat aaagtcattc aaaagctttc aaacttaaga   1440
aaaaataatg aagctattgc ctatggaacc acagaaattt tatacagcac aaatgatgta   1500
ctggtctttta aaagacagtt ctatgataaa caagtaattg tagcggtaaa ccgacaaccg   1560
gatcaaacgt ttaccattcc ggagttagat acgactcttc cagtaggaac ctatagtgat   1620
gtactgggtg gactgttata tgggagttca atgagcgtaa ataatgtcaa cggtcaaaac   1680
```

-continued

```
aaaatttcta gctttacctt gtctggagga gaggtcaatg tctggtcgta taacccatca    1740
ttggggactt taactccaag gattggcgac gttatttcca ccatgggacg tcccggtaat    1800
accgtttaca tttacggtac tggattagga ggaagcgtaa cagtcaaatt cggttctact    1860
gttgctactg tggtgtcaaa cagcgatcaa atgattgagg ctatagttcc aaacactaat    1920
cctggaattc aaaatattac agttacaaaa ggatctgtaa ccagtgatcc tttccgatat    1980
gaggtcctat ccggcgatca ggtgcaagta attttcatg tgaatgccac aacgaattgg     2040
ggggaaaaca tttatgttgt cggaaacatt ccagagttgg gaagctggga tccgaaccaa    2100
tcgtctgagg cgatgttaaa tccgaactat ccagaatggt tcttgccagt gagtgtgccc    2160
aagggagcta cttttgaatt caagtttatc aaaaaagata caatggaaa tgtcatttgg     2220 gaaagcagga gcaacagagt atttaccgca ccgaacagtt cgaccggtac tattgacacc    2280
cctttatatt tttgggataa ctaa                                           2304
```

<210> SEQ ID NO 7
<211> LENGTH: 767
<212> TYPE: PRT
<213> ORGANISM: Geobacillus sp.

<400> SEQUENCE: 7

```
Met Trp Lys Val Pro Lys Phe Ile Lys Gln Ser Tyr Leu Val Phe Leu
 1               5                  10                  15

Leu Ala Leu Leu Leu Tyr Ser Ser Phe Gly Phe Ser Phe Ser Arg Thr
             20                  25                  30

Glu Ala Thr Thr Ser Thr Gly Ala Leu Gly Pro Val Thr Pro Lys Asp
         35                  40                  45

Thr Ile Tyr Gln Ile Val Thr Asp Arg Phe Phe Asp Gly Asp Pro Ser
     50                  55                  60

Asn Asn Lys Pro Pro Gly Phe Asp Pro Thr Leu Phe Asp Asp Pro Asp
 65                  70                  75                  80

Gly Asn Asn Gln Gly Asn Gly Lys Asp Leu Lys Leu Tyr Gln Gly Gly
                 85                  90                  95

Asp Phe Gln Gly Ile Ile Asp Lys Ile Pro Tyr Leu Lys Asn Met Gly
            100                 105                 110

Ile Thr Ala Val Trp Ile Ser Ala Pro Tyr Glu Asn Arg Asp Thr Val
        115                 120                 125

Ile Glu Asp Tyr Gln Ser Asp Gly Ser Ile Asn Arg Trp Thr Ser Phe
    130                 135                 140

His Gly Tyr His Ala Arg Asn Tyr Phe Ala Thr Asn Lys His Phe Gly
145                 150                 155                 160

Thr Met Lys Asp Phe Ile Arg Leu Arg Asp Ala Leu His Gln Asn Gly
                165                 170                 175

Ile Lys Leu Val Ile Asp Phe Val Ser Asn His Ser Ser Arg Trp Gln
            180                 185                 190

Asn Pro Thr Leu Asn Phe Ala Pro Glu Asp Gly Lys Leu Tyr Glu Pro
        195                 200                 205

Asp Lys Asp Ala Asn Gly Asn Tyr Val Phe Asp Ala Asn Gly Glu Pro
    210                 215                 220

Ala Asp Tyr Asn Gly Asp Gly Lys Val Glu Asn Leu Leu Ala Asp Pro
225                 230                 235                 240

His Asn Asp Val Asn Gly Phe Phe His Gly Leu Gly Asp Arg Gly Asn
                245                 250                 255

Asp Thr Ser Arg Phe Gly Tyr Arg Tyr Lys Asp Leu Gly Ser Leu Ala
```

```
            260                 265                 270
Asp Tyr Ser Gln Glu Asn Ala Leu Val Val Glu His Leu Glu Lys Ala
        275                 280                 285

Ala Lys Phe Trp Lys Ser Lys Gly Ile Asp Gly Phe Arg His Asp Ala
    290                 295                 300

Thr Leu His Met Asn Pro Ala Phe Val Lys Gly Phe Lys Asp Ala Ile
305                 310                 315                 320

Asp Ser Asp Ala Gly Gly Pro Val Thr His Phe Gly Glu Phe Phe Ile
                325                 330                 335

Gly Arg Pro Asp Pro Lys Tyr Asp Glu Tyr Arg Thr Phe Pro Glu Arg
            340                 345                 350

Thr Gly Val Asn Asn Leu Asp Phe Glu Tyr Phe Arg Ala Ala Thr Asn
        355                 360                 365

Ala Phe Gly Asn Phe Ser Glu Thr Met Ser Ser Phe Gly Asp Met Met
    370                 375                 380

Ile Lys Thr Ser Asn Asp Tyr Ile Tyr Glu Asn Gln Thr Val Thr Phe
385                 390                 395                 400

Leu Asp Asn His Asp Val Thr Arg Phe Arg Tyr Ile Gln Pro Asn Asp
                405                 410                 415

Lys Pro Tyr His Ala Ala Leu Ala Val Leu Met Thr Ser Arg Gly Ile
            420                 425                 430

Pro Asn Ile Tyr Tyr Gly Thr Glu Gln Tyr Leu Met Pro Ser Asp Ser
        435                 440                 445

Ser Asp Ile Ala Gly Arg Met Phe Met Gln Thr Ser Thr Asn Phe Asp
    450                 455                 460

Glu Asn Thr Thr Ala Tyr Lys Val Ile Gln Lys Leu Ser Asn Leu Arg
465                 470                 475                 480

Lys Asn Asn Glu Ala Ile Ala Tyr Gly Thr Thr Glu Ile Leu Tyr Ser
                485                 490                 495

Thr Asn Asp Val Leu Val Phe Lys Arg Gln Phe Tyr Asp Lys Gln Val
            500                 505                 510

Ile Val Ala Val Asn Arg Gln Pro Asp Gln Thr Phe Thr Ile Pro Glu
        515                 520                 525

Leu Asp Thr Thr Leu Pro Val Gly Thr Tyr Ser Asp Val Leu Gly Gly
    530                 535                 540

Leu Leu Tyr Gly Ser Ser Met Ser Val Asn Val Asn Gly Gln Asn
545                 550                 555                 560

Lys Ile Ser Ser Phe Thr Leu Ser Gly Gly Glu Val Asn Val Trp Ser
                565                 570                 575

Tyr Asn Pro Ser Leu Gly Thr Leu Thr Pro Arg Ile Gly Asp Val Ile
            580                 585                 590

Ser Thr Met Gly Arg Pro Gly Asn Thr Val Tyr Ile Tyr Gly Thr Gly
        595                 600                 605

Leu Gly Gly Ser Val Thr Val Lys Phe Gly Ser Thr Val Ala Thr Val
    610                 615                 620

Val Ser Asn Ser Asp Gln Met Ile Glu Ala Ile Val Pro Asn Thr Asn
625                 630                 635                 640

Pro Gly Ile Gln Asn Ile Thr Val Thr Lys Gly Ser Val Thr Ser Asp
                645                 650                 655

Pro Phe Arg Tyr Glu Val Leu Ser Gly Asp Gln Val Gln Val Ile Phe
            660                 665                 670

His Val Asn Ala Thr Thr Asn Trp Gly Glu Asn Ile Tyr Val Val Gly
        675                 680                 685
```

-continued

Asn Ile Pro Glu Leu Gly Ser Trp Asp Pro Asn Gln Ser Ser Glu Ala
690                 695                 700

Met Leu Asn Pro Asn Tyr Pro Glu Trp Phe Leu Pro Val Ser Val Pro
705                 710                 715                 720

Lys Gly Ala Thr Phe Glu Phe Lys Phe Ile Lys Lys Asp Asn Asn Gly
            725                 730                 735

Asn Val Ile Trp Glu Ser Arg Ser Asn Arg Val Phe Thr Ala Pro Asn
            740                 745                 750

Ser Ser Thr Gly Thr Ile Asp Thr Pro Leu Tyr Phe Trp Asp Asn
            755                 760                 765

<210> SEQ ID NO 8
<211> LENGTH: 733
<212> TYPE: PRT
<213> ORGANISM: Geobacillus sp.

<400> SEQUENCE: 8

Thr Thr Ser Thr Gly Ala Leu Gly Pro Val Thr Pro Lys Asp Thr Ile
1               5                   10                  15

Tyr Gln Ile Val Thr Asp Arg Phe Phe Asp Gly Asp Pro Ser Asn Asn
            20                  25                  30

Lys Pro Pro Gly Phe Asp Pro Thr Leu Phe Asp Pro Asp Gly Asn
        35                  40                  45

Asn Gln Gly Asn Gly Lys Asp Leu Lys Leu Tyr Gln Gly Gly Asp Phe
50                  55                  60

Gln Gly Ile Ile Asp Lys Ile Pro Tyr Leu Lys Asn Met Gly Ile Thr
65                  70                  75                  80

Ala Val Trp Ile Ser Ala Pro Tyr Glu Asn Arg Asp Thr Val Ile Glu
                85                  90                  95

Asp Tyr Gln Ser Asp Gly Ser Ile Asn Arg Trp Thr Ser Phe His Gly
            100                 105                 110

Tyr His Ala Arg Asn Tyr Phe Ala Thr Asn Lys His Phe Gly Thr Met
        115                 120                 125

Lys Asp Phe Ile Arg Leu Arg Asp Ala Leu His Gln Asn Gly Ile Lys
130                 135                 140

Leu Val Ile Asp Phe Val Ser Asn His Ser Ser Arg Trp Gln Asn Pro
145                 150                 155                 160

Thr Leu Asn Phe Ala Pro Glu Asp Gly Lys Leu Tyr Glu Pro Asp Lys
                165                 170                 175

Asp Ala Asn Gly Asn Tyr Val Phe Asp Ala Asn Gly Glu Pro Ala Asp
            180                 185                 190

Tyr Asn Gly Asp Gly Lys Val Glu Asn Leu Leu Ala Asp Pro His Asn
        195                 200                 205

Asp Val Asn Gly Phe Phe His Gly Leu Gly Asp Arg Gly Asn Asp Thr
210                 215                 220

Ser Arg Phe Gly Tyr Arg Tyr Lys Asp Leu Gly Ser Leu Ala Asp Tyr
225                 230                 235                 240

Ser Gln Glu Asn Ala Leu Val Val Glu His Leu Glu Lys Ala Ala Lys
                245                 250                 255

Phe Trp Lys Ser Lys Gly Ile Asp Gly Phe Arg His Asp Ala Thr Leu
            260                 265                 270

His Met Asn Pro Ala Phe Val Lys Gly Phe Lys Asp Ala Ile Asp Ser
        275                 280                 285

Asp Ala Gly Gly Pro Val Thr His Phe Gly Glu Phe Phe Ile Gly Arg
290                 295                 300

```
Pro Asp Pro Lys Tyr Asp Glu Tyr Arg Thr Phe Pro Glu Arg Thr Gly
305                 310                 315                 320

Val Asn Asn Leu Asp Phe Glu Tyr Phe Arg Ala Ala Thr Asn Ala Phe
            325                 330                 335

Gly Asn Phe Ser Glu Thr Met Ser Ser Phe Gly Asp Met Met Ile Lys
        340                 345                 350

Thr Ser Asn Asp Tyr Ile Tyr Glu Asn Gln Thr Val Thr Phe Leu Asp
    355                 360                 365

Asn His Asp Val Thr Arg Phe Arg Tyr Ile Gln Pro Asn Asp Lys Pro
370                 375                 380

Tyr His Ala Ala Leu Ala Val Leu Met Thr Ser Arg Gly Ile Pro Asn
385                 390                 395                 400

Ile Tyr Tyr Gly Thr Glu Gln Tyr Leu Met Pro Ser Asp Ser Ser Asp
            405                 410                 415

Ile Ala Gly Arg Met Phe Met Gln Thr Ser Thr Asn Phe Asp Glu Asn
        420                 425                 430

Thr Thr Ala Tyr Lys Val Ile Gln Lys Leu Ser Asn Leu Arg Lys Asn
    435                 440                 445

Asn Glu Ala Ile Ala Tyr Gly Thr Thr Glu Ile Leu Tyr Ser Thr Asn
450                 455                 460

Asp Val Leu Val Phe Lys Arg Gln Phe Tyr Asp Lys Gln Val Ile Val
465                 470                 475                 480

Ala Val Asn Arg Gln Pro Asp Gln Thr Phe Thr Ile Pro Glu Leu Asp
            485                 490                 495

Thr Thr Leu Pro Val Gly Thr Tyr Ser Asp Val Leu Gly Leu Leu
        500                 505                 510

Tyr Gly Ser Ser Met Ser Val Asn Asn Val Asn Gly Gln Asn Lys Ile
    515                 520                 525

Ser Ser Phe Thr Leu Ser Gly Gly Glu Val Asn Val Trp Ser Tyr Asn
530                 535                 540

Pro Ser Leu Gly Thr Leu Thr Pro Arg Ile Gly Asp Val Ile Ser Thr
545                 550                 555                 560

Met Gly Arg Pro Gly Asn Thr Val Tyr Ile Tyr Gly Thr Gly Leu Gly
            565                 570                 575

Gly Ser Val Thr Val Lys Phe Gly Ser Thr Val Ala Thr Val Val Ser
        580                 585                 590

Asn Ser Asp Gln Met Ile Glu Ala Ile Val Pro Asn Thr Asn Pro Gly
    595                 600                 605

Ile Gln Asn Ile Thr Val Thr Lys Gly Ser Val Thr Ser Asp Pro Phe
610                 615                 620

Arg Tyr Glu Val Leu Ser Gly Asp Gln Val Gln Val Ile Phe His Val
625                 630                 635                 640

Asn Ala Thr Thr Asn Trp Gly Glu Asn Ile Tyr Val Val Gly Asn Ile
            645                 650                 655

Pro Glu Leu Gly Ser Trp Asp Pro Asn Gln Ser Ser Glu Ala Met Leu
        660                 665                 670

Asn Pro Asn Tyr Pro Glu Trp Phe Leu Pro Val Ser Val Pro Lys Gly
    675                 680                 685

Ala Thr Phe Glu Phe Lys Phe Ile Lys Lys Asp Asn Asn Gly Asn Val
690                 695                 700

Ile Trp Glu Ser Arg Ser Asn Arg Val Phe Thr Ala Pro Asn Ser Ser
705                 710                 715                 720

Thr Gly Thr Ile Asp Thr Pro Leu Tyr Phe Trp Asp Asn
            725                 730
```

```
<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
gccggagctc atgactacat ctacaggagc tttag                          35

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
gccgtctaga ttagttatcc caaaaatata aag                            33
```